United States Patent [19]

Grollier et al.

[11] Patent Number: 4,880,618
[45] Date of Patent: Nov. 14, 1989

[54] USE OF PARTIALLY ACETYLATED POLYVINYL ALCOHOL AS A FOAMING AGENT IN COMPOSITIONS IN THE FORM OF AEROSOLS

[75] Inventors: Jean F. Grollier, Paris; Claude Dubief, Le Chesnay; Jean Mondet, Drancy, all of France

[73] Assignee: L'Oreal, Paris, France

[21] Appl. No.: 235,775

[22] Filed: Aug. 23, 1988

Related U.S. Application Data

[63] Continuation of Ser. No. 50,026, May 15, 1987, abandoned.

[30] Foreign Application Priority Data

May 16, 1986 [LU] Luxembourg .................... 86430

[51] Int. Cl.$^4$ .......................... A61K 7/11; C09K 3/30
[52] U.S. Cl. ................................ 424/43; 424/DIG. 1
[58] Field of Search .................... 424/40–45, 424/DIG. 1

[56] References Cited

U.S. PATENT DOCUMENTS

| | | | |
|---|---|---|---|
| 2,854,377 | 9/1958 | Elias | 424/44 |
| 3,136,692 | 6/1964 | Brandelin | 424/44 |
| 3,417,180 | 12/1968 | Sirota et al. | 424/47 |
| 3,912,665 | 10/1975 | Spitzer et al. | 260/2.5 E |
| 3,948,817 | 4/1976 | Grothoff | 424/45 X |
| 4,007,005 | 2/1977 | Patel | 424/DIG. 1 X |
| 4,165,367 | 8/1979 | Chakrabarti | 424/DIG. 1 X |
| 4,223,009 | 9/1980 | Chakrabarti | 424/DIG. 1 X |
| 4,376,114 | 3/1983 | Jacquet et al. | 424/DIG. 1 X |
| 4,552,754 | 11/1985 | Muramatsu et al. | 424/DIG. 1 X |

FOREIGN PATENT DOCUMENTS

| | | |
|---|---|---|
| 0128226 | 12/1984 | European Pat. Off. |
| 2477414 | 9/1981 | France |
| 856403 | 12/1960 | United Kingdom |
| 1306508 | 2/1973 | United Kingdom |
| 1462632 | 1/1977 | United Kingdom |
| 1486619 | 9/1977 | United Kingdom |
| 1595649 | 8/1981 | United Kingdom |
| 2114580 | 8/1983 | United Kingdom |

OTHER PUBLICATIONS

Weitz, P., "Vinyl Copolymer in the Cosmetic Cosmos", J. Soc. Cosmetic Chemistry 11, 291 (1960).
Encyclopedia of Polymer Science & Technology, vol. 15, p. 662, lines 1–2 (1971), Interscience Publishers.

*Primary Examiner*—Nancy A. B. Swisher
*Attorney, Agent, or Firm*—Fleit, Jacobson, Cohn, Price, Holman & Stern

[57] ABSTRACT

Use of partially acetylated polyvinyl alcohol as a foaming agent in compositions in the form of aerosols.

Use as a single or additional foaming agent in aqueous compositions for treating the skin or the hair, in the form of an aerosol foam, of partially acetylated polyvinyl alcohol containing at least some units of formulae (I) and (II)

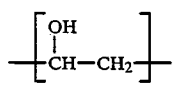

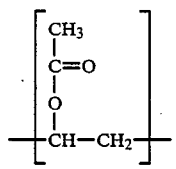

in which the units of formula (II) are present in proportions of greater than or equal to 3 mol % with respect to the totality of units in the polymer, this polymer possessing a viscosity at a concentration of 4% in water at 20° C. of between 0.005 and 0.065 Pa.s.

31 Claims, No Drawings

USE OF PARTIALLY ACETYLATED POLYVINYL ALCOHOL AS A FOAMING AGENT IN COMPOSITIONS IN THE FORM OF AEROSOLS

This application is a continuation of application Ser. No. 050,026, filed May 15, 1987, now abandoned.

The present invention relates to the use of partially acetylated polyvinyl alcohol in compositions which are intended for the treatment of the hair or the skin and pressurized as aerosols.

Cosmetic compositions pressurized in aerosol devices, under conditions such as to form a foam when they emerge, are well-known and have been used for some years in the treatment of the hair or the skin. For ease of reference, such compositions will be called "aerosol foams".

These foams enable a good distribution of the cosmetic compositions to be obtained on the hair, and they are, furthermore, easy to use and more economical as regards the products.

For the cosmetic treatment of the hair, agents are used which may have various effects, such as improvement of the sheen, of the feel, of disentangling and of shape-retention, or provision of an anti-grease or anti-dandruff effect, or alternatively are used for strengthening the hair, altering its styling or conditioning it. The term "cosmetic treatment" embraces, without being limiting, the production of one or more of these results.

The term "hair conditioning" is also frequently used, this term encompassing the production of good disentangling, good shape-retention, a pleasant feel and an attractive appearance of the hair.

A cosmetic treatment of the skin refers to a treatment which consists, for example, in softening the skin or making it supple or firm, or which leads to the production of an anti-grease or moisturizing effect.

The objective pursued by the Applicant is to be able to offer compositions used for the treatment of the hair or the skin in the form of aerosol foams.

The foaming agents traditionally used for forming foams of this type, such as anionic, nonionic or amphoteric surfactants, often tend to modify the properties of the treatment products with which they are mixed, or modify the appearance or the feel of the hair. Thus, some foaming agents are incompatible with certain cosmetic agents and destabilized compositions, leading to a modification of the cosmetic properties of the hair, or else they generate foams having a greasy feel, which is undesirable in a cosmetic treatment. Moreover, some of these agents possess the disadvantage of foaming for an excessively long time when the wet hair is combed; this is more especially the case when a treatment is not followed by rinsing and is applied on hair which has been wrung free of excess water after shampooing.

The Applicant has now discovered a new foaming agent which enables aerosol foams to be obtained which satisfy a set of criteria, such as firmness, expansion, stability, creaminess, and non-greasy feel, which are especially advantageous in cosmetic treatment. This foaming agent is essentially neutral towards the components of the composition as regards their cosmetic properties, and it is, moreover, compatible with treatment agents.

The Applicant has found, moreover, that the use of this foaming agent, in combination with products which already enable aerosol foams to be obtained, such as polymers, for example, leads, surprisingly, to the production of the foam which is creamier, more expanded, firmer and less greasy to the touch.

This foaming agent consists of partially acetylated polyvinyl alcohol.

Polyvinyl alcohol, also known as PVA, is a polyhydroxylated nonionic water-soluble polymer which has been known for a long time, and it is produced by hydrolysis (alkaline alcoholysis of polyvinyl acetate). A polyvinyl alcohol derived from polyvinyl acetate is considered to be completely hydrolysed when the degree of hydrolysis is equal to or greater than 98 mol %.

For ease of reference, a polyvinyl alcohol originating from hydrolysed polyvinyl acetate having a degree of hydrolysis equal to or less than 97%, and which consequently contains acetyl groups, is referred to in the description and the claims as "partially acetylated polyvinyl alcohol".

The degree of hydrolysis of partially acetylated polyvinyl alcohols is generally between 60 and 97 mol %.

The foaming properties, from an aerosol pack, of partially acetylated polyvinyl alcohol are especially surprising when it is realised that nonionic polymers, which are generally used, even in aerosol compositions, are virtually devoid of foaming properties, and that polyvinyl alcohol originating from completely hydrolysed polyvinyl acetate (degree of hydrolysis greater than 97%) does not enable an aerosol foam to be formed.

Non-acetylated polyvinyl alcohols have already been used in cosmetics, in particular as gelling agents for the production of hair-care gels. Moreover, the use of partially acetylated polyvinyl alcohol in cosmetics has also been recommended, especially in gelatin-based compositions for the purpose of obtaining a transparent film which enables the appearance and the feel of greasy hair to be improved.

The subject of the invention is hence the use of partially acetylated polyvinyl alcohol as a single or additional foaming agent in cosmetic aerosol compositions.

Another subject of the invention consists of cosmetic compositions pressurized in an aerosol device containing at least partially acetylated polyvinyl alcohol for the purpose of forming a foam after expansion in the air.

The subject of the invention also consists of a process for treatment of the hair employing a foam at least containing, by way of a single or additional foaming agent, partially acetylated polyvinyl alcohol.

Other subjects of the invention will emerge on reading the description and the examples which follow.

The partially acetylated polyvinyl alcohol used as a single or additional foaming agent in compositions for cosmetic treatment of the skin or the hair, in the form of an aerosol foam, is characterized in that it contains at least some units of formulae (I) and (II):

in which the units for formula (II) are present in proportions of greater than or equal to 3 mol % with respect to the totality of units in the polymer, and preferably in proportions of less than or equal to 40%. This polymer results from the partial hydrolysis of polyvinyl acetate, and its degree of hydrolysis is less than or equal to 97% and its viscosity at a concentration of 4% in water at 20° C. is between 0.005 and 0.065 Pa.s (DIN 53,015).

The polymer defined above should give, moreover, a foam having a density, after expansion in the air foam an aerosol device, of less than or equal to 0.3 g/cm³ at 20° C.

The density of the foam defined above is measured according to the method described below:

A 1% strength aqueous solution of partially acetylated polyvinyl alcohol is packaged in an aerosol can consisting of an integrally made aluminium can having an ogival neck (45×128) with a Precision P 73 valve without a dip tube and having an axial diffuser button for a conical cup (021550). The aerosol can is filled to the extent of 90 g of 1% strength solution of partially acetylated polyvinyl alcohol and 10 g of Freon F 114/F 12 (43:57) propellant gas sold by DUPONT DE NEMOURS. The handling operation is performed 24 hours after pressurization of the aerosols in a chamber conditioned at 20° C.±1° C., the material and the sample being at the same temperature. A cylindrical cup is weighed empty (let its weight be P 1) and then filled directly with the foam produced by the aerosol. Each aerosol can is well shaken before use, so as to emulsify the propellant gas.

For a uniform distribution of the foam in the cup, the aerosols are used head downwards in a regular rotatory movement.

As soon as the expansion of the foam is complete, the latter is immediately and rapidly levelled off using a broad spatula, and the cup is weighed again (let its weight be P 2).

The density of the foam is determined according to the following formula:

$$\text{density at } 20° \text{ C.} = \frac{P2 - P1}{V}$$

(V is the volume of the cup). Three determinations are performed for each polymer, the value adopted being the mean value of these determinations (in g/cm³).

Among the partially acetylated polyvinyl alcohols which may be used according to the invention, there may be mentioned the commercial products sold, for example, under the name "RHODOVIOL" by RHONE POULENC, "POLYVIOL" by WACKER, "POVAL" by KURARAY, "MOWIOL" by HOECHST and "AIRVOL" by AIR PRODUCT.

According to the invention, polyvinyl alcohols originating from partially hydrolysed polyvinyl acetate and having a degree of hydrolysis of between 80 and 90%, that is say containing 10 to 20 mol % of units of formula II with respect to the units of the polymer and possessing a high viscosity, are preferably used. Among these preferred partially acetylated polyvinyl alcohols, there may be mentioned the products sold under the name MOWIOL 4088 by HOECHST, which has a degree of hydrolysis of 87.7%±1 and a viscosity at a concentration of 4% in water, according to DIN standard 53,015, of 0.040 Pa.s; the product marketed under the name "RHODOVIOL 25 140" by RHONE POULENC, which has a degree of hydrolysis of 89% and a viscosity at a concentration of 4% in water of 0.025 Pa.s; and the product marketed under the name "MOWIOL 4-98" by HOECHST, etherified with 2.24 mol % of bromooctane and the degree of hydrolysis of which is of the order of 96%.

The partially acetylated polyvinyl alcohol which is used according to the invention is employed in proportions of between 0.05 and 8% by weight relative to the total weight of the composition, and preferably between 0.2 and 3%.

The composition according to the invention is intended to be used for the treatment of the hair or the skin in the form of a foam, from an aerosol device in which it is packaged under pressure; this composition comprises at least one partially acetylated polyvinyl alcohol corresponding to the above definition, in a cosmetically acceptable aqueous medium containing one or more products intended for the cosmetic treatment of the hair and/or the skin.

The aqueous cosmetic medium can contain, in addition to water, any cosmetically acceptable solvent chosen, in particular, from monohydric alcohols such as alkanols having 1 to 8 carbon atoms, for example ethanol, isopropanol, benzyl alcohol or phenylethyl alcohol, polyhydric alcohols such as alkylene glycols, for example ethylene glycol, or glycol ethers such as mono-, di- and triethylene glycol alkyl ethers, for example ethylene glycol monomethyl ether, ethylene glycol monoethyl ether or diethylene glycol monoethyl ether, used alone or mixed. When they are present, these solvents are used in proportions of less than or equal to 50% by weight, and preferably 30%, relative to the total weight of the composition, and in amounts such as to enable a foam having a density of less than or equal to 0.3 g/cm³ at 20° C. in this cosmetically acceptable medium to be obtained with the partially acetylated polyvinyl alcohol defined above. The measurement is performed in the same device and under the same conditions as those defined above for the choice of the partially acetylated polyvinyl alcohol, water being replaced by the aqueous cosmetic medium adopted.

The agents intended for the cosmetic treatment of the hair can be agents which foam or do not foam when they are used separately in the cosmetic medium not containing the partially acetylated polyvinyl alcohol.

A cosmetic agent is considered not to foam when it does not form a foam or when the density of the aerosol foam is greater than 0.3 g/cm³ at 20° C. according to the test described above for the partially acetylated polyvinyl alcohol.

These treatment agents can be cationic, anionic, nonionic or amphoteric in nature.

By cationic treatment agents, there are understood molecular compounds or polymers comprising one or more primary, secondary or tertiary amine or quaternary ammonium groups in their molecules. Such agents generally show a great affinity for the keratin of the hair, and more especially when this keratin has been degraded by chemical or physical treatments or by atmospheric agents.

Among these compounds, the following may be mentioned more especially:

(I) Cationic surfactants such as salts of fatty amines, for example alkylamine acetates, quaternary ammonium salts such as alkyldimethylbenzylammonium, alkyltrimethylammonium, alkyldimethylhydroxyethylammonium, dimethyldistearylammonium and dimethyldilaurylammonium chlorides or bromides, acetyldimethyldodecylammonium chloride, alkylamidoethyltrimethylammonium methosulphates, lactates of N,N-dimethylamino or N,N-diethylamino polyoxyethylcarboxylate oxyethyleneated, for example, with 4 moles of ethylene oxide, alkylpyridinium salts such as 1-(2-hydroxyethyl)carbamoylmethylpyridinium chloride, N-lauryl-(colaminoformylmethyl)pyridinium chloride, imidazoline derivatives such as alkylimidazolines; amine oxides, alkyldimethylamine oxides and alkylaminoethyldimethylamine oxides; and the cationic derivatives corresponding to the formula:

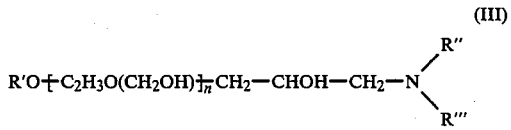
(III)

in which R' denotes a saturated or unsaturated linear or branched alkyl radical or an alkylaryl radical having a linear or branched chain containing from 8 to 22 carbon atoms, R" and R'" denote lower hydroxyalkyl radicals or alkylene radicals joined to one another to form a heterocyclic system, and n is a number between 0.5 and 10.

Other cationic surfactants which may be used are the water-dispersible compounds of the formula (IV):

(IV)

in which: (a) When $R_1$ denotes a group of formula:

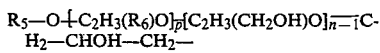

in which
$R_5$ denotes a saturated or unsaturated, linear or branched aliphatic radical, $R_6$ is an alkyl radical, a linear or branched alkoxymethyl radical or a linear alkenyloxy radical,
p denotes an integer or decimal number from 1 to 2.5,
n denotes an integer or decimal number from 2 to 20,
$R_2$ denotes an alkyl or hydroxyalkyl radical having from 1 to 3 carbon atoms and $R_3$ and $R_4$, which may be identical or different, denote an alkyl or hydroxyalkyl radical having from 1 to 3 carbon atoms or alternatively form, with the nitrogen atom to which they are attached, a 5 or 6-membered heterocyclic system;
$X^\ominus$ denotes an anion and preferably a methylsulphate, methanesulphonate, p-toluenesulphonate, bromide, chloride or iodide anion.

(b) When $R_2$ and $R_3$ denote a methyl radical, $R_1$ and $R_4$ have the following meanings:
(i) $R_1$ and $R_4$ denote a linear aliphatic radical;
(ii) or alternatively $R_1$ denotes a saturated linear aliphatic radical and $R_4$ denotes a methyl or benzyl radical;
(iii) or alternatively $R_1$ denotes an alkylamidopropyl ($C_{14}$–$C_{22}$ alkyl) radical and $R_4$ denotes an alkyl acetate ($C_{12}$–$C_{16}$ alkyl) group;
$X^\ominus$ denotes an anion such as a halide or $CH_3SO_4^-$.

(c) When $R_1$ denotes an alkylamidoethyl and/or alkenylamidoethyl group in which the alkyl and/or alkenyl radical containing from 14 to 22 carbon atoms is derived from tallow fatty acids and $R_2$ and $R_3$ form with the nitrogen a substituted heterocyclic system of the 4,5-dihydroimidazole type,
$R_4$ denotes a $C_1$–$C_4$ alkyl;
$X^\ominus$ denotes a $CH_3SO_4$—anion.

Bis(quaternary ammonium) derivatives having two lipophilic chains of formula (V):

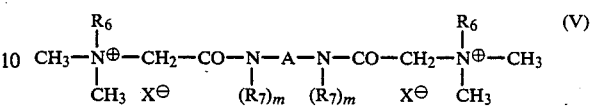
(V)

in which $R_6$ denotes a linear or branched, saturated or unsaturated aliphatic group having from 8 to 22 carbon atoms or a mixture of these groups or a mixture of lipophilic chains derived from natural products having from 8 to 30 carbon atoms; A denotes a group —(CH$_2$)—$_n$ in which n denotes an integer from 1 to 18 and $R_7$ denotes H, and m=1; and A can also form a heterocyclic group with the nitrogen atoms to which it is attached, in which case m=0 and $X^\ominus$ denotes an anion derived from an inorganic or organic acid.

These compounds are described in the Applicant's French Pat. No. 2,464,710.

Among the more especially preferred cationic surfactants, the following may be mentioned:
(1) the compounds of formula:

(VI)

in which
$R_8$ and $R_{11}$ each denote a mixture of alkenyl and/or alkyl radicals derived from tallow fatty acids having 14 to 22 carbon atoms, $R_9$ and $R_{10}$ denote a methyl radical and $X^\ominus$ denotes a $Cl^\ominus$ ion
or alternatively $R_8$ denotes a $C_{18}$ alkyl radical, $R_{11}$ denotes a benzyl radical, $R_9$ and $R_{10}$ denote a methyl radical and $X^-$ denotes $Cl^-$;

(2) bis(quaternary ammonium) derivatives bearing an ester group, such as the product sold under the name "AMONYL DM" by SEPPIC (3) the bis(quarternary ammonium) derivative corresponding to the formula:

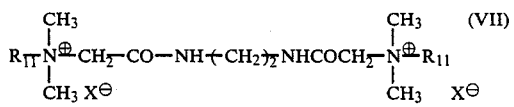
(VII)

in which $R_{11}$ is a tallow chain and $X^\ominus$ is $Cl^\ominus$;

(4) the (tallow alkyl) trimethylammonium chloride sold in solution in isopropyl alcohol under the name "ARQUAD T 50" by ARMAK;

(5) tetradecyltrimethylammonium bromide;

(6) (cocamidopropyl)dimethylacetamidoammonium chloride corresponding to the formula:

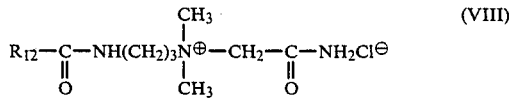
(VIII)

where the radical $R_{12}$ is a coconut chain;

(7) the (acylamidopropyl)dimethylethylammonium ethylsulphate in which the acyl group is derived from lanolin fatty acids, sold under the name "LANOQUAT 50" and classified under the name QUATERNIUM 33 in the CFTA dictionary;

(8) (γ-gluconamidopropyl)dimethylhydroxyethylammonium chloride sold under the name "CERAPHYL 60" by VAN DYK and classified under the name QUATERNIUM 22 in the CTFA dictionary;

(9) trimethyldocosylammonium chloride.

(II) Cationic polymers which are chosen from polymers containing primary, secondary, tertiary and/or quaternary amine groups forming part of the polymer chain or directly attached to the latter, having a molecular weight of between 500 and approximately 5,000,000 and approximately 1,000 and 3,000,000.

Among these polymers, there may be mentioned, more especially, quaternized proteins, quaternized polysiloxanes and polymers of the polyamine, polyaminoamide or poly(quaternary ammonium) type. These polymers are preferably present in proportions of between 0.25 and 3% by weight relative to the total weight of the composition.

A. The quaternized proteins are, in particular, chemically modified polypeptides bearing quaternary ammonium groups at the end of the chain or grafted onto the latter. Among these proteins, there may be mentioned, in particular:

collagen hydrolysates bearing triethylammonium groups, such as the products sold under the name "QUATPRO E" by MAYBROOK and designated "Triethonium Hydrolysed Collagen Ethosulfate" in the CTFA dictionary;

the collagen hydrolysates bearing trimethylammonium or dimethylstearylammonium chloride groups sold under the name "QUAT-PRO S" by MAYBROOK and designated "Steartrimonium Hydrolyzed Collagen" in the CTFA dictionary;

hydrolysates of animal proteins bearing dimethylbenzylammonium groups, such as the products sold under the name "CROTEIN BTA" by CRODA and designated "Benzyltrimonium hydrolyzed animal protein" in the CTFA dictionary;

protein hydrolysates bearing, on the polypeptide chain, quaternary ammonium groups containing at least one alkyl radical having from 1 to 18 carbon atoms.

Among these protein hydrolysates, there may be mentioned, inter alia:

CROQUAT L, in which the polypeptide chain has an average molecular weight of approximately 2,500 and in which the quaternary ammonium group contains a $C_{12}$ alkyl group;

CROQUAT M, in which the polypeptide chain has an average molecular weight of approximately 2,500 and in which the quaternary ammonium group contains a $C_{10}-C_{18}$ alkyl group;

CROQUAT S, in which the polypeptide chain has an average molecular weight of approximately 2,700 and in which the quaternary ammonium group contains a $C_{18}$ alkyl groups;

CROTEIN Q, in which the polypeptide chain has an average molecular weight of the order of 12,000 and in which the quaternary ammonium group contains at least one alkyl group having from 1 to 18 carbon atoms.

These different products are sold by CRODA.

Other quaternized proteins are those corresponding to the formula:

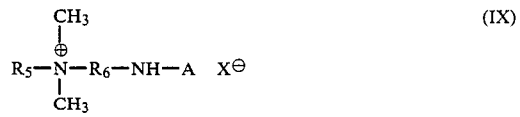

(IX)

in which A denotes a protein residue derived from hydrolysates of collagen protein, $R_5$ denotes a lipophilic group containing up to 30 carbon atoms, $R_6$ denotes an alkylene group having 1 to 6 carbon atoms and $X^\ominus$ denotes an anion derived from an organic or inorganic acid, these proteins having a molecular weight of between 1,500 and 10,000 and preferably between 2,000 and 5,000. The preferred products are those sold under the name "LEXEIN QX 3000" by INOLEX, referred to in the CFTA dictionary as "Cocotrimonium Collagen Hydrolysate".

B. Another family of cationic polymers consists of silicone cationic polymers. Among these polymers, the following may be mentioned:

(a) the quaternized polysiloxanes designated "Amodimethicone" in the CTFA dictionary and corresponding to the formula:

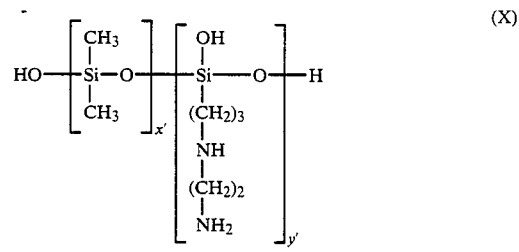

(X)

in which x' and y' are integers depending on the molecular weight which is generally between 5,000 and 10,000;

(b) the silicone cationic polymers corresponding to the formula:

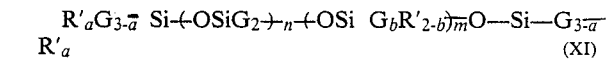

(XI)

in which

G is a hydrogen atom, a phenyl group, OH, or a $C_1-C_8$ alkyl group and preferably methyl, a denotes 0 or an integer from 1 to 3, and preferably 0, b denotes 0 or 1, and preferably 1, the sum (n+m) is an integer from 1 to 2,000, and preferably from 50 to 150, n being able to denote a number from 0 to 1,999 and preferably from 49 to 149, and m being able to denote an integer from 1 to 2,000 and preferably from 1 to 10;

R' is a monovalent radical of formula $C_qH_{2q}L$, in which q is a number from 2 to 8 and L is chosen from the groups:

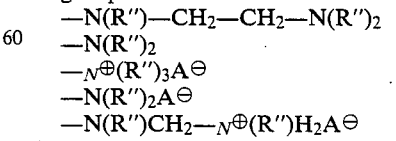

in which formulae R" can denote hydrogen, phenyl, benzyl, a monovalent saturated hydrocarbon radical and preferably an alkyl radical having from 1 to 20 carbon atoms and $A^\ominus$ denotes a halide ion such as chloride, bromide, iodide or fluoride.

An especially advantageous product which falls within this definition is the polymer designated "trimethylsilylamodimethicone", corresponding to the formula:

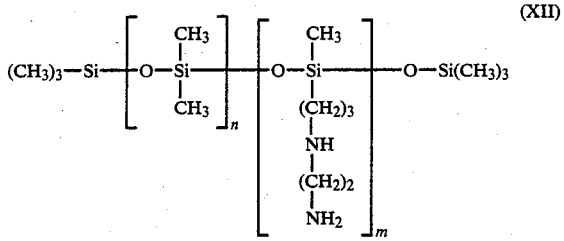
(XII)

in which n and m have the meanings given above (formula X). Such polymers are described in Patent Application EP-A-95,238;

(c) the silicone cationic polymers corresponding to the formula:

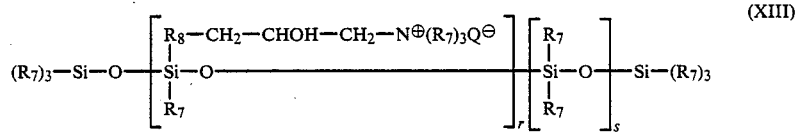
(XIII)

in which $R_7$ denotes a monovalent hydrocarbon radical having from 1 to 18 carbon atoms, and especially an alkyl or alkenyl radical and preferably methyl;

$R_8$ denotes a divalent hydrocarbon radical, preferably a $C_1$-$C_{18}$ alkylene radical or a $C_1$-$C_{18}$, and preferably $C_1$-$C_8$, divalent alkylenoxy radical;

$Q^\ominus$ is a halide ion, preferably chloride;

r denotes an average statistical value from 2 to 20 and preferably from 2 to 8;

s denotes an average statistical value from 20 to 200 and preferably from 20 to 50.

Such polymers are described more especially in U.S. Pat. No. 4,185,087.

An especially preferred polymer which falls within this class is the polymer sold by UNION CARBIDE under the name "UCAR SILICONE ALE 56", which is characterized by a flashpoint of 60° C. according to the standard ASTDM-93 and a viscosity at a concentration of 35% of active substance and at 25° C. of 0.011 Pa.s, and by a total base number of 0.24 meq/g.

When these silicone polymers are employed, an especially advantageous embodiment is their joint use with nonionic surfactants and optionally cationic surfactants. It is possible to use, for example, in the compositions according to the invention, the commercial product sold under the name "DC 929 CATIONIC EMULSION" by DOW CORNING, which comprises amodimethicone of the formula (X), a cationic surfactant corresponding to the formula:

(XIV)

in which $R_9$ denotes a mixture of alkenyl and/or alkyl radicals having from 14 to 22 carbon atoms and derived from tallow fatty acids, and a nonionic surfactant of formula:

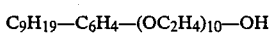

known under the name "NONOXYNOL 10".

Another composition which may be used in this embodiment of the invention is the composition containing the product sold under the name "DOW CORNING Q2 7224" by DOW CORNING, containing, in combination, trimethylsilylamodimethicone of formula (XII), a nonionic surfactant of formula:

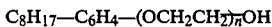

where n=40 also known as octoxynol-40, another nonionic surfactant of formula:

where n=6 also known as isolaureth-6, and glycol.

C. The polymers of the polyamine, polyaminoamide or poly(quaternary ammonium) type which may be used according to the present invention are described, in particular, in the Applicant's French Pat. Nos. 82/07,996 or 84/04,475.

Among these polymers, the following may be mentioned:

(1) Vinylpyrrolidone/dialkylaminoalkyl acrylate or methacrylate copolymers, quaternized or otherwise, such as the products sold under the name of "GAFQUAT" by GAF CORPORATION, for example "GAFQUAT 734 or 755" or alternatively the products designated "COPOLYMER 845, 958 and 937". These polymers are described in detail in French Pat. Nos. 2,077,143 and 2,393,573.

(2) The cellulose ether derivatives containing quaternary ammonium groups described in French Pat. No. 1,492,597 and in particular the products marketed under the designations "JR" (JR 400, JR 125, JR 30M) or "LR" (LR 400, LR 30M) by UNION CARBIDE CORPORATION. The polymers are also defined in the CTFA dictionary as quaternary ammonium derivatives of hydroxyethylcellulose which has reacted with an epoxide substituted with a trimethylammonium group.

(3) Cationic cellulose derivatives, such as cellulose copolymers or cellulose derivatives grafted with a water-soluble quaternary ammonium monomer, described in greater detail in U.S. Pat. No. 4,131,576, such as hydroxyalkylcelluloses, for example hydroxymethyl-, hydroxyethyl- or hydroxypropylcellulose grafted with a (methacryloylethyl)trimethylammonium, (methacrylamidopropyl)trimethylammonium or dimethyldiallylammonium salt.

The marketed products corresponding to this definition are, more especially, the products sold under the names "CELQUAT L 200" and "CELQUAT H 100" by NATIONAL STARCH.

(b 4) The cationic polysaccharides described, more especially, in U.S. Pat. Nos. 3,589,578 and 4,031,307, and more especially the product marketed under the name "JAGUAR C. 13 S" sold by MEYHALL.

(5) Polymers consisting of piperazinyl units and of divalent alkylene or hydroxyalkylene radicals having linear or branched chains optionally interrupted by oxygen, sulphur or nitrogen atoms or by aromatic or heterocyclic rings, as well as the oxidation and/or quaternization products of these polymers. Such polymers are described in French Pat. Nos. 2,162,025 and 2,280,361.

(6) The water-soluble polyaminoamides prepared, in particular, by polycondensation of an acidic compound with a polyamine. These polyaminoamides can be crosslinked with an epihalohydrin, a diepoxide, a dianhydride, an unsaturated anhydride, a doubly unsaturated derivative, a bis(halohydrin), a bis(azetidinium) compound, a bis(haloacyldiamine) or a bis(alkyl halide), or alternatively with an oligomer resulting from the reaction of a bifunctional compound which is reactive towards a bis(halohydrin), a bis(azetidinium) compound, a bis(haloacyldiamine), a bis(alkyl halide), an epihalohydrin, a diepoxide or a doubly unsaturated derivative; the crosslinking agent being used in proportions ranging from 0.025 to 0.35 mol per amine group of the polyaminoamide.

These polyaminopolyamides can be alkylated or, if they contain one or more tertiary amine groups, quaternized. Such polymers are described, in particular, in French Pat. Nos. 2,252,840 and 2,368,508.

(7) The polyaminoamide derivatives resulting from the condensation of polyalkylenepolyamines with polycarboxylic acids, followed by an alkylation with bifunctional agents. There may be mentioned, for example, the adipic acid/dialkylaminohydroxyalkyl dialkylenetriamine polymers in which the alkyl radical contains from 1 to 4 carbon atoms and preferably denotes methyl, ethyl or propyl. Such polymers are described in French Pat. No. 1,583,363.

Among these derivatives, there may be mentioned, more especially, the adipic acid/dimethylaminohydroxypropyl/diethylenetriamine polymers sold under the names "CARTARETIN F, F$_4$ or F$_8$" by SANDOZ.

(8) The polymers obtained by reaction of a polyalkylenepolyamine containing two primary amine groups and at least one secondary amine group with a dicarboxylic acid chosen from diglycollic acid and saturated aliphatic dicarboxylic acids having from 3 to 8 carbon atoms; the mole ratio between the polyalkylenepolyamine and the dicarboxylic acid being between 0.8:1 and 1.4:1; and the resulting polyaminoamide being reacted with epichlorohydrin in a mole ratio of epichlorohydrin with respect to the secondary amine group of the polyaminoamide of between 0.5:1 and 1.8:1. Such polymers are described, in particular, in U.S. Pat. Nos. 3,227,615 and 2,961,347.

Polymers of this type are marketed, in particular, under the name "HERCOSETT 57" by HERCULES INCORPORATED or alternatively under the name "PD 170" or "DELSETTE 101" by HERCULES in the case of the adipic acid/epoxypropyl/diethylenetriamine copolymer.

(9) Cyclopolymers having a molecular weight of 20,000 to 3,000,000, such as homopolymers containing, as the main constituent of the chain, units corresponding to the formula (XV) or (XV')

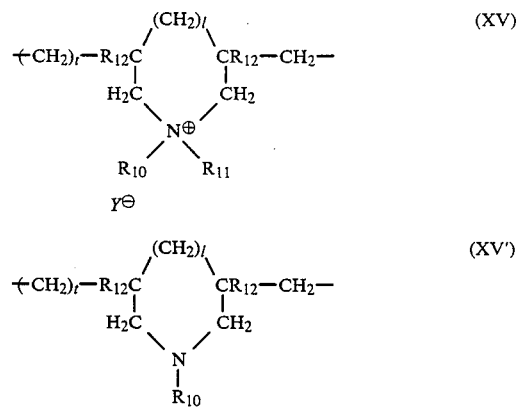

$l$ and $t$ are equal to 0 or 1, and the sum $l+t=1$, $R_{12}$ denotes hydrogen or methyl, $R_{10}$ and $R_{11}$ denote, independently of one another, an alkyl group having from 1 to 22 carbon atoms, a hydroxyalkyl group in which the alkyl group preferably has from 1 to 5 carbon atoms, or a lower amidoalkyl group, and/or $R_{10}$ and $R_{11}$ can denote, together with the nitrogen atom to which they are attached, heterocyclic groups such as piperidinyl or morpholinyl, as well as copolymers containing units of formula (XV) or (XV') and units derived from acrylamide or from diacetoneacrylamide; $Y^\ominus$ is an anion such as bromide, chloride, acetate, borate, citrate, tartrate, bisulphate, bisulphite, sulphate, phosphate. Among the polymers defined above, there may be mentioned, more especially, the homopolymer of dimethyldiallylammonium chloride sold under the name MERQUAT 100 having a molecular weight of less than 100,000, and the copolymer of dimethyldiallylammonium chloride and acrylamide having a molecular weight of more than 500,000 and sold under the name MERQUAT 550 by MERCK.

These polymers are described, more especially, in French Pat. No. 2,080,759 and its certificate of addition No. 2,190,406.

(10) The poly(quaternary ammonium) polymer containing repeated units corresponding to the formula:

in which $R_{13}$ and $R_{14}$, $R_{15}$ and $R_{16}$, which may be identical or different, denote aliphatic, alicyclic, or arylaliphatic radicals containing from 1 to 20 carbon atoms or lower hydroxyalkylaliphatic radicals, or alternatively $R_{13}$ and $R_{14}$ and $R_{15}$ and $R_{16}$, together or separately, form, with the nitrogen atoms to which they are attached, heterocyclic systems optionally containing a second hereto atom other than nitrogen, or alternatively $R_{13}$, $R_{14}$, $R_{15}$ and $R_{16}$ denote a linear or branched $C_1$–$C_6$ alkyl radical substituted with a nitrile, ester, acyl or amide group or with a group

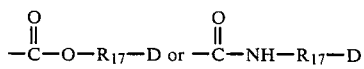

where $R_{17}$ is an alkylene and D a quaternary ammonium group.

$A_2$ and $B_2$ denote polymethylene groups containing from 2 to 20 carbon atoms, which may be linear or branched, saturated or unsaturated and may contain, linked to or inserted in the main chain, one or more aromatic rings, or one or more oxygen or sulphur atoms, or sulphoxide, sulphone, disulphide, amino, alkylamino, hydroxyl, quaternary ammonium, ureido, amide or ester groups, and $X^\ominus$ denotes an anion derived from an inorganic or organic acid.

$A_2$ and $R_{13}$ and $R_{15}$ can form a piperazine ring with the two nitrogen atoms to which they are attached; in addition, if $A_2$ denotes a saturated or unsaturated, linear or branched alkylene or hydroxyalkylene radical, $B_2$ can also denote a group:

—(CH₂)ₙ—CO—D—OC—(CH₂)ₙ— in which D denotes:

(a) a glycol residue of formula: —O—Z—O— where Z denotes a linear or branched hydrocarbon radical or a group corresponding to the formulae:

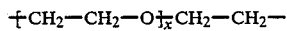

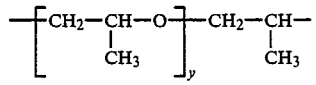

where x and y denote an integer from 1 to 4 representing a definite and unique degree of polymerization, or any number from 1 to 4 representing an average degree of polymerization;

(b) a bis(secondary diamine) residue such as a piperazine derivative;

(c) a bis(primary diamine) residue of formula:

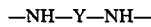
—NH—Y—NH— where Y denotes a linear or branched hydrocarbon radical or alternatively the divalent radical

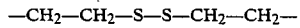
—CH₂—CH₂—S—S—CH₂—CH₂—

(d) a ureylene group of formula:

—NH—CH—NH—;

$X^\ominus$ is an anion such as chloride or bromide.

These polymers have a molecular mass which is generally between 1,000 and 100,000.

Polymers of this type are described, in particular, in French Pat. Nos. 2,320,330, 2,270,846, 2,316,271, 2,336,434 and 2,413,907, and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) The poly(quaternary ammonium) polymers consisting of units of formula:

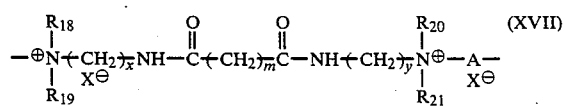

in which $R_{18}$, $R_{19}$, $R_{20}$ and $R_{21}$, which may be identical or different, denote a hydrogen atom or a methyl, ethyl, propyl, β-hydroxyethyl, β-hydroxypropyl or —CH₂CH₂(OCH₂CH₂)ₚOH radical, where p equals 0 and an integer between 1 and 6, with the proviso that $R_{18}$, $R_{19}$, $R_{20}$ and $R_{21}$ do not simultaneously denote a hydrogen atom; x and y, which may be identical or different, are integers between 1 and 6;

m equals 0 or an integer between 1 and 34,

X denotes a halogen atom,

A denotes a radical of a dihalide and preferably denotes

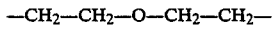
—CH₂—CH₂—O—CH₂—CH₂—

Such compounds are described in greater detail in patent application Ser. No. EP-A-122,324.

(12) The homopolymers or copolymers derived from acrylic or methacrylic esters or amides and containing the units:

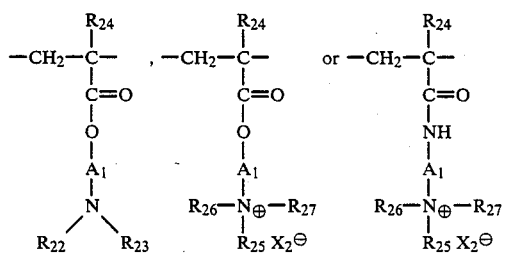

in which $R_{24}$ denotes H or CH₃, $A_1$ is a linear or branched alkyl group having from 1 to 6 carbon atoms or a hydroxyalkyl group having from 1 to 4 carbon atoms, $R_{25}$, $R_{26}$ and $R_{27}$, which may be identical or different, denote an alkyl group having from 1 to 18 carbon atoms or a benzyl radical, $R_{22}$ and $R_{23}$ denote hydrogen or an alkyl group having from 1 to 6 carbon atoms, and $X_2^-$ denotes a methosulphate anion or a halide such as chloride or bromide.

The comonomer or comonomers which may be used belong(s) to the following families: acrylamide, methacrylamide, diacetoneacrylamide, acrylamide and methacrylamide substituted on the nitrogen with lower alkyl groups, acrylic or methacrylic acids or their esters, vinylpyrrolidone and vinyl esters.

Among these compounds, there may be mentioned the copolymer of acrylamide and dimethylaminoethyl methacrylate quaternized with dimethyl sulphate and sold under the name "HERCOFLOC" by HERCULES, the copolymer of acrylamide and methacryloyloxyethyltrimethylammonium chloride—described in patent application Ser. No. EP-A-80,976—and sold under the name "BINA QUAT P100" by CIBA GEIGY, or the poly(methacrylamidopropyltrimethylammonium chloride) sold under the name "POLYMAPTAC" by TEXACO CHEMICALS.

(13) Quaternary polymers of vinylpyrrolidone and vinylimidazole, such as, for example, the products marketed under the names LUVIQUAT FC 905, FC 550 and FC 370 by BASF.

(14) Polyamines such as Polyquart H sold by Henkel, classified under the name "POLYETHYLENE GLYCOL (15) TALLOW POLYAMINE" in the CTFA dictionary.

Other cationic polymers which may be used according to the invention are polyalkyleneimines, in particular polyethyleneimines, polymers containing vinylpyridine or vinylpyridinium units, condensates of polyamines and epichlorohydrin, quaternary polyureylenes and chitin derivatives.

The polymers which are especially preferred in the compositions according to the invention are as follows:
the polymer containing the units of formula:

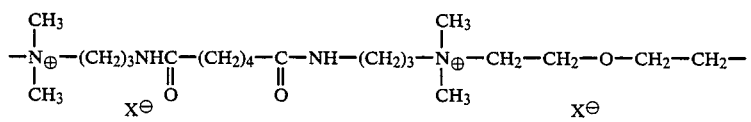

$X^-$ being a halide, sold under the name "MIRAPOL AD 1" by MIRANOL;
the polymer containing the units of formula:

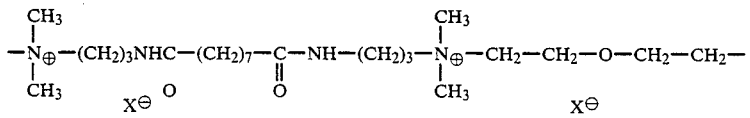

$X^-$ being a halide, sold under the name "MIRAPOL AZ1" by MIRANOL;
poly(methacrylamidopropyltrimethylammonium chloride) sold under the name "POLYMAPTAC" by TEXACO CHEMICALS;
the quaternized polymer of the ionene type described in the applicant's French Pat. No. 2,270,846, and more especially that containing the units:

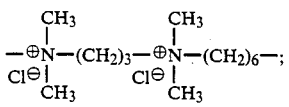

the dimethyldiallylammonium cyclopolymers sold under the name "MERQUAT 100" and "MERQUAT 550" by MERCK;
quaternary vinylpyrrolidone and vinylimidazole polymers, such as those sold under the names "LUVIQUAT FC 905, FC 550 and FC 370" by BASF;
vinylpyrrolidone/dialkylaminoalkyl acrylate or methacrylate copolymers, quaternized or otherwise, such as the products sold under the names "COPOLYMER 845", "GAFQUAT 734 or 755" by GAF;
polymers of quaternary cellulose ethers, such as those sold under the designations "JR" such as, for example, JR 125, JR 400 and JR 30 M, and "LR" such as LR 400 and LR 30 by UNION CARBIDE CORPORATION;
cationic cellulose derivatives, such as the products sold under the names "CELQUAT L 200" and "CELQUAT H 100" by NATIONAL STARCH;
quaternary ammonium polymers of the type described in U.S. Pat. No. 4,157,388 and more especially the polymer containing units of formula:

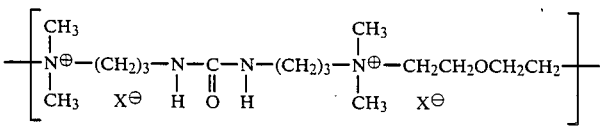

$X^-$ being a halide ion, sold under the name "MIRAPOL A 15" by MIRANOL; and
the poly(dimethylbutenylammonium chloride)-$\alpha,\omega$-bis(triethanolammonium chloride) sold under the name "ONAMER M" by ONYX INTERNATIONAL.

For further details, the different cationic polymers are also described in French Pat. Nos. 2,383,660 and 2,542,997.

The treatment agents can also be anionic in nature, and more especially anionic polymers used alone or in combination with the cationic treatment agents defined above. An especially preferred embodiment consists in using, as a combination, cationic polymers and anionic polymers as described in French Pat. Nos. 2,542,997, 2,544,000, 2,521,427 and 2,383,660.

The anionic polymers contain carboxylic, sulphonic or phosphoric acid units, and have a molecular weight of between 500 and 5,000,000 and preferably between 1,000 and 3 million. Among these polymers, the following may be mentioned more especially.

alkali metal salts of polyhydroxycarboxylic acids, such as the products sold under the name "HYDROGEN F" by HENKEL;

homopolymers of acrylic or methacrylic acid, preferably not crosslinked, or their salts, such as, for example, the products sold under the names "VERSICOL E or K" by ALLIED COLLOID or the product sold under the name "DARVAN No. 7" by VAN DER BILT;

methacrylic acid/$C_1$-$C_4$ alkyl methacrylate copolymers;

copolymers derived from maleic, fumaric and itaconic acids or anhydrides and from vinyl esters, vinyl ethers, vinyl halides, phenylvinyl derivatives, acrylic acid or acrylates, these copolymers optionally being partially or completely esterified and described more especially in U.S. Pat. Nos. 2,047,398, 2,723,248 and 2,102,213 and British Pat. No. 839,805. Among these copolymers, there may be mentioned, more especially, the products sold under the names "GANTREZ", "AN" or "ES" by GENERAL ANILINE or "EMA 1325" by MONSANTO. Other polymers belonging to this class are copolymers of maleic, fumaric and itaconic anhydrides and of an allyl or methallyl ester and optionally of acrylamide, methacrylamide, an alpha-olefin, acrylic or methacrylic acids or their esters, or vinylpyrrolidone; the anhydride functions being monoesterified or monoamidated as described in published French patent application Ser. Nos. 76/13,929 and 76/20,917;

terpolymers consisting of 10 to 91% by weight of vinyl acetate, 3 to 20% by weight of an unsaturated carboxylic acid, preferably chosen from crotonic acid, allyloxyacetic acid, allyloxypropionic acid and vinylacetic acid and 4 to 60% by weight of at least one vinyl, allyl or methallyl ester of an alpha-(ring-substituted) carboxylic acid. Among these polymers, there may preferably be mentioned the vinyl acetate/crotonic acid/vinyl tert-butylbenzoate (65:10:25) copolymer as described in French Pat. No. 2,439,798;

vinyl acetate/crotonic acid copolymers grafted onto polyethylene glycol, such as the product sold by HOECHST under the name "ARISTOFLEX A";

vinyl acetate/crotonic acid/vinyl neodecanoate terpolymers, such as the product sold under the name "RESYN 28-29-30" NATIONAL STARCH;

polyacrylamides containing carboxylate groups, such as the product sold under the name "CYANAMER A 370" by AMERICAN CYANAMID.

The polymers containing sulphonic units are chosen, more especially, from the sodium salts of polystyrenesulphonic acid, such as the products sold by NATIONAL STARCH under the names "FLEXAN 500" and "FLEXAN 130", having a molecular weight of approximately 500,000 and 800,000 respectively;

salts of polyacrylamido-sulphonic acids such as polyacrylamidomethylpropanesulphonic acid, for example the product sold under the name "COSMEDIA POLYMER HSP 1180" by HENKEL;

salts of a polymer containing alkylnaphthalenesulphonic acid units, such as the product sold under the name "DARVAN No. 1," by VAN DER BILT;

calcium or sodium lignosulphonates, such as the products sold under the name "MARASPERSE C 21" by CAN CO, and those $C_{10}$-$C_{14}$ compounds sold by AVEBENE;

sodium polyvinyl sulphonates having a molecular weight of between 1,000 and 100,000.

Nonionic treatment agents can consist of nonionic polymers having a molecular weight of between 500 and 3,000,000 and can be used alone or mixed with anionic and/or cationic polymers mentioned above.

Among these nonionic polymers, the following may be mentioned:
polyvinylpyrrolidone,
vinylpyrrolidone/vinyl acetate copolymers,
polyacrylamides,
polyethylene glycols,
water-soluble polyamides containing from 50 to 100% of units of formula:

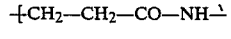

and from 0 to 50% of units of formula

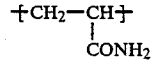

described more especially in U.S. Pat. No. 4,082,730 and in French Pat. No. 2,508,795, and preferably poly($\beta$-alanines).

Amphoteric polymers can also be used as treatment agents, alone or in combination with the cationic derivatives or the polymers mentioned above. These polymers have a molecular weight of 500 to 3,000,000 and are chosen, in particular, from polymers containing units A AMERICAN and B statistically distributed in the polymer chain, where A denotes a unit derived from a monomer containing at least one basic nitrogen atom and B denotes a unit derived from an acidic monomer containing one or more carboxyl or sulphonyl groups, A and/or B also being able to denote groups derived from zwitterionic monomers of carboxybetaine or sulphobetaine.

A and B can also denote cationic polymer chains containing primary, secondary, tertiary or quaternary amine groups, in which chains one of the amine groups bears a carboxyl or sulphonyl group linked via a hydrocarbon radical; or alternatively A and B form part of a chain of a polymer containing $\alpha,\beta$-dicarboxyethylene units in which one of the carboxyl groups has been reacted with a polyamine containing one or more primary or secondary amine groups.

Especially preferred amphoteric polymers are chosen from the following:

the polymers resulting from the reaction of a polyaminoamide, obtained by polycondensation of adipic acid and diethylenetriamine in equimolar amounts, and crosslinked with epichlorohydrin in the proportion of 11 mol of crosslinking agent for 100 secondary amine groups of the polyaminoamide, the product being alkylated with propane sultone to the extent of 50%, or alternatively with sodium chloroacetate;

the polymer obtained by polycondensation of epichlorohydrin and piperazine in the presence of sodium hydroxide, and betainized;

the octylacrylamide/acrylate/butylaminoethylmethacrylate copolymer sold under the name "AMPHOMER" by NATIONAL STARCH;

methylmethacrylate/carboxymethyldimethylammonioethyl methacrylate copolymer;

($C_1$-$C_{18}$) alkyl methacrylate/carboxymethyldimethylammoniomethyl methacrylate copolymer having a molecular weight of 70,000 to 90,000, such as the product sold under the name "AMPHOSET" by MITSUBISHI PETROCHEMICAL Co. LTD. or under the name "AMERSETTE" by AMERCHOL;

the polymers derived from chitosan described, in particular, in French Pat. No. 2,137,684 and containing units corresponding to the formulae:

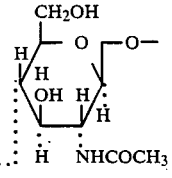

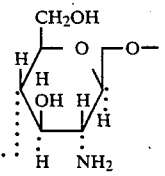

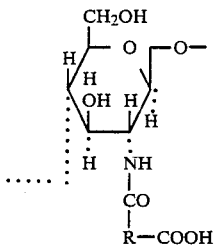

The polymer preferably contains 0 to 20% of unit A, 40 to 50% of unit B and 40 to 50% of unit C in which R denotes an alkylene radical, and preferably —CH$_2$—CH$_2$;

the polyaspartic acid derivatives corresponding to the formula:

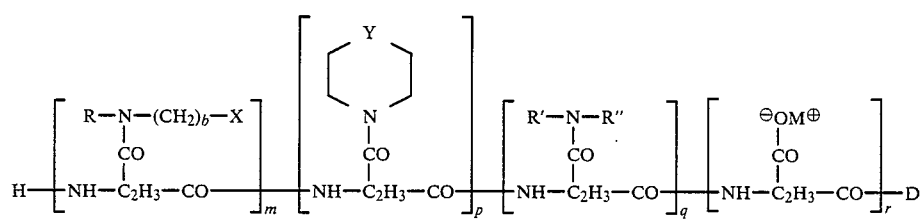

in which R denotes a hydrogen atom or a lower alkyl radical, b is an integer varying from 2 to 6, X denotes a group —NR$_I$(R$_{II}$) or a group —N$^\oplus$R$_I$(R$_{II}$)(R$_{III}$) Z$^\ominus$ where R$_I$, R$_{II}$ and R$_{III}$, which may be identical or different, denote a hydrogen atom, an alkyl group having 1 to 18 carbon atoms or an alkenyl group having 2 to 18 carbon atoms, or R$_I$ and R$_{II}$ denotes, with the nitrogen atom to which they are attached, a 6-membered ring which can contain another hetero atom, and Z$^{63}$ denotes an anion derived from an organic or inorganic acid, Y denotes an oxygen atom, a methylene group, a group NR''' or a group N$^{61}$(R''')(R'''') Z$^{63}$, where R'''' and R''''', which may be identical or different, denote a hydrogen atom, an alkyl group having 1 to 18 carbon atoms or alkenyl group having 2 to 18 carbon atoms and Z$_1^\ominus$ denotes an anion derived from an organic or inorganic acid, R' denoting a hydrogen atom, a lower hydroxyalkyl group, a lower hydroxyalkyloxyalkyl group, an alkyl group having 1 to 18 carbon atoms or an alkenyl group having 2 to 18 carbon atoms, R'' denotes a hydrogen atom, a lower hydroxyalkyl group or a lower alkyl group, M denotes a hydrogen atom, an alkali metal atom or an alkaline earth metal half-atom, or alternatively M$^\oplus$ denotes an ammonium ion, and D denotes a group

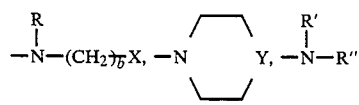

or —O$^\ominus$M$^\ominus$ m and p, q and r denoting integers including 0, such that the sum m+p+q+r varies from 15 to 500, m and p being able to be zero simultaneously (a) only when q is other than 0 and R' denotes a hydroxyalkyl group, and (b) not when q equals 0.

The compounds are described in French Pat. No. 2,403,076.

The especially preferred compounds according to the invention and containing partially acetylated polyvinyl alcohol by way of a foaming agent are compositions comprising:

(1) the combination of a water-dispersible cationic surfactant, a water-soluble quaternized protein and a silicone cationic polymer as defined above; such a combination is described, in particular, in French patent application No. 2,562,794;

(2) a combination as described in French patent application No. 2,548,019, containing a water-dispersible cationic surfactant, a water-soluble quaternized cationic polymer of the ionene type defined, in particular, in group 10 of the cationic polymers above and a silicone cationic polymer;

(3) a composition comprising, in combination in a cosmetically acceptable aqueous medium, a sodium polyvinylsulphonate and a condensate of piperazine and epichlorohydrin;

(4) a composition containing an amphoteric polymer (XVIII) such as the methyl methacrylate/carboxymethyldimethylammonioethyl methacrylate described, more especially, in the Applicant's French Pat. No. 2,470,596, with either a cellulose ether derivative comprising quaternary ammonium groups, of the type described in French Pat. No. 1,492,597 and sold under the designations, "JR" or "LR" by UNION CARBIDE, or alternatively a cationic cellulose derivative as described in U.S. Pat. No. 4,131,576, for example products sold under the names "CELQUAT L 200" and "CELQUAT H 100" by NATIONAL STARCH;

the homopolymers of dimethyldiallylammonium chloride or copolymers of dimethyldiallylammonium chloride with acrylamide sold, respectively, under the names "MERQUAT 100" and MERQUAT 550" by MERCK;

vinylpyrrolidone/diaminoalkyl acrylate or methacrylate copolymers, quaternized or otherwise, such as, for example, the products sold under the names "GAFQUAT 734 or 755";

quaternary polymers of vinylpyrrolidone and vinylimidazole, such as, for example, the products sold under the names "LUVIQUAT FC 905", "FC 970" and "FC 550" by BASF;

(5) compositions containing a vinylpyrrolidone/diethylaminoethyl methacrylate copolymer, such as, more especially, the product sold under the name "COPOLYMER 845" by GAF;

(6) compositions containing a vinylpyrrolidone/diethylaminoethyl methacrylate copolymer, such as the product sold under the name "COPOLYMER 845" by GAF, with the cationic polymers derived from cellulose ether, cellulose derivatives, the homo- and copolymers of dimethyldiallylammonium chloride or the quaternary polymers of vinylpyrrolidone and vinylimidazole, defined above.

Another preferred embodiment of the invention consists of a composition containing, in aqueous or aqueous-alcoholic dispersion, the partially acetylated polyvinyl alcohol defined above, with a water-soluble polyamide of the type described in U.S. Pat. No. 4,082,730 and Belgian Pat. No. 893,738, or with cationic polymers chosen from the quaternary cellulose ether derivatives, cationic cellulose derivatives, dimethyldiallylammonium chloride polymers and quaternary vinylpyrrolidone/imidazole polymers defined above, or alternatively with the vinylpyrrolidone/diaminoalkyl acrylate or methacrylate copolymers, quaternized or otherwise.

The cosmetic treatment agents are present in the compositions according to the invention in proportions which can vary from 0.01 to 10% by weight relative to the total weight of the composition, and preferably between 0.05 and 6% by weight.

These compositions can also contain electrolytes such as alkali metal salts, for example sodium, potassium or lithium salts. These salts are preferably chosen from the sulphates and halides, such as chloride or bromide, or the salts or organic acids, especially acetate or lactate. It is also possible to use alkaline earth metal salts and more especially calcium, magnesium or strontium carbonate, silicate, nitrate, acetate, gluconate, pantothenate and lactate. These electrolytes are present in concentrations which vary between 0.25 and 8% by weight relative to the total weight of the composition.

The compositions according to the invention can contain other ingredients customarily used in cosmetics, such as perfumes, colourings whose function is to colour the composition itself, the hair or the skin, preservatives, sequestering agents, anti-grease, anti-seborrhoeic and anti-dandruff agents, silicones, demulcents, sunscreens and peptizing agents, as well as, optionally, anionic, nonionic or amphoteric surfactants, or mixtures thereof, in proportions of less that 10% and preferably less than 7%.

It is understood that, when such ingredients are present, the composition must enable a foam having a density equal to or less than 0.3 g/cm$^3$ at 20° C. in this cosmetically acceptable medium, as described above, to be obtained with the partially acetylated polyvinyl alcohol defined above.

The ingredients must enable, in particular, a foam possessing the density stated above to be obtained with the partially acetylated polyvinyl alcohol, applying the method of determination of the density which is defined above, the aqueous solution in this case containing the ingredient in question in the desired proportions, in addition to the partially acetylated polyvinyl alcohol in proportions of 1%.

The compositions according to the invention preferably do not contain solid absorbent materials, in particular clays such as kaolinites and attapulgites and especially those which have a particle size of less than 30 microns.

These compositions are packaged in pressurized devices as aerosols in the presence of propellant gases which are generally present in proportions not exceeding 25% relative to the total weight of the composition, and preferably 15%. By way of a propellant gas, it is possible to use carbon dioxide, nitrogen, nitrous oxide, volatile hydrocarbons such as butane, isobutane, propane and mixtures thereof, or non-hydrolyzable chlorinated and/or fluorinated halogenated hydrocarbons, such as the compounds sold under the names "FREON" by DU PONT DE NEMOURS and more especially fluorochlorohydrocarbons such as dichlorodifluoromethane "FREON 12" or dichlorotetrafluoroethane or "FREON 114". These propellant agents can be used alone or mixed, for example a "FREON 114/FREON 12" mixture in proportions of between 40:60 and 80:20.

The compositions according to the invention can take various forms, such as lotions, emulsions or dispersions, which, after distribution from the aerosol device, form the foams for application on the hair or the skin.

The foams distributed from aerosol devices and having the compositions defined above may be applied in the form of after-shampoo compositions, of a product to be rinsed applied before or after dyeing or bleaching, before or after permanent waving or straightening, as a setting or blow-drying agent or in the form of a product whose application is not followed by rinsing, such as styling foams. These compositions can also be used for restructuring, permanent waving or dyeing or bleaching the hair. Their pH is generally between 3 and 10 and is adjusted using an alkalinizing or acidifying agent customarily used in cosmetics.

When the foams according to the invention are intended to be used for hair styling or shaping or setting, they generally comprise, in aqueous or aqueous-alcoholic dispersion, the partially acetylated polyvinyl alcohol as well as one or more polymers and, more especially, the nonionic polymers defined above.

When the foams according to the invention are used for permanent waving, they contain, in addition to the partially acetylated polyvinyl alcohol and the cosmetic polymers, either a reducing agent or an oxidizing agent, according to whether they constitute the first or the second phase of the permanent-waving process. These compositions are applied according to the traditional technique, which consists in applying initially on the hair the composition containing a reducing agent and, after rinsing the hair where appropriate, in applying a composition containing an oxidizing agent.

Another epecially preferred embodiment consists of employing the foam as a foam to be rinsed, mainly applied before or after shampooing. This foam generally contains, in solution or in emulsion, the partially acetylated polyvinyl alcohol and one or more cosmetic treatment agents which have also been mentioned above.

Another embodiment of the invention consists in using a composition containing treatment agents which are non-foaming in the aqueous medium in the absence of the partially acetylated polyvinyl alcohol, and applying this composition in the form of a foam as a result of the presence of the partially acetylated polyvinyl alcohol.

The examples which follow are intended to illustrate the invention without thereby being limiting in nature.

EXAMPLE 1

A non-rinsed aerosol foam having the following composition is prepared:

| | |
|---|---|
| Amphoteric polymer sold under the name "AMPHOSET" by MITSUBISHI | 0.5 g AS |
| Copolymer of hydroxyethylcellulose grafted with diallyldimethylammonium chloride, sold under the name "CELQUAT L 200" by NATIONAL STARCH | 0.5 g AS |
| Polyvinyl alcohol sold under the name "MOWIOL 4088" by HOECHST | 0.2 g |
| Ethyl alcohol qs 10% (by volume) | |
| Spontaneous pH: 7.4 | |

Preservative, perfume qs
Water qs                                                100 g 90 g of the said composition is introduced into an integrally made aluminium aerosol can without a dip tube, equipped with a PRECISION P 73 valve, with 10 g of a FREON F 114/F 12 mixture in the ratio 43:57.

The foam is applied on clean hair which has been wrung free of excess water. The hair disentangles readily, and is soft to the touch. After drying, the hair is lively and is easy to style. The foam obtained possesses, according to the test described above, a density $d = 0.061$ g/cm$^3$ at 20° C.

EXAMPLE 2

A non-rinsed aerosol foam having the following composition is prepared:

| | |
|---|---|
| Condensate of epichlorohydrin with a condensate of adipic acid and diethylenetriamine, prepared according to Example 1a of French Patent No. 2,252,840 | 1 g AS |
| Quaternized polyvinyloyrrolidone copolymer having an MW of 100,000, sold under the name "GAFQUAT 734" by GENERAL ANILINE | 0.5 g AS |
| Polyvinyl alcohol sold under the name "POVAL-PVA 217" by KURARAY | 0.8 g |
| Ethyl alcohol qs 10% (by volume) | |
| Spontaneous pH: 9 | |
| Preservative, perfume qs | |
| Water qs | 100 g |

The composition is packaged as described in Example 1.

The foam obtained is applied on permanent-waved hair which has been wrung free of excess water. The wet hair disentagles readily and is soft to the touch. After drying, the hair is soft, smooth and lively. The foam obtained possesses a density $d = 0.065$ g/cm$^3$ at 20° C.

EXAMPLE 3

The following styling foam is prepared:

| | |
|---|---|
| Cationic polymer described and prepared according to French Patent 2,270,846, consisting of repeated units of formula: | 0.3 g AS |

$$\left[ \begin{array}{cc} CH_3 & CH_3 \\ | & | \\ {}^\oplus N-(CH_2)_3- & {}^\oplus N-(CH_2)_6 \\ | & | \\ CH_3\ Cl^\ominus & CH_3\ Cl^\ominus \end{array} \right]$$

| | |
|---|---|
| Polyvinylpyrrolidone/vinyl acetate copolymer sold by GAF | 0.3 g AS |
| Polyvinyl alcohol sold under the name "RHODOVIOL 25/140" by RHONE POULENC | 1 g |
| Ethyl alcohol qs 10% (by volume) | |
| Spontaneous pH: 6.1 | |
| Preservative, perfume qs | |
| Water qs | 100 g |

The composition is packaged as described in Example 1; the foam is applied on clean hair which has been wrung free of excess water. The wet hair disentangles easily. The foam obtained possesses a density $d = 0.070$ g/cm$^3$ at 20° C.

EXAMPLE 4

The following styling foam is prepared:

| | |
|---|---|
| Condensate of adipic acid and diethylenetriamine, crosslinked with the compound of formula: | 0.3 g AS |

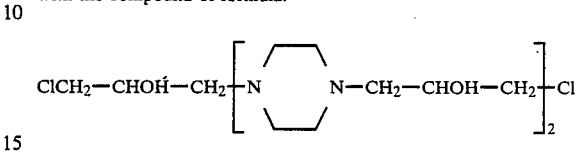

| | |
|---|---|
| prepared according to Example Xb of French Patent No. 2,368,508 | |
| Sodium polyvinylsulphonate | 0.2 g |
| Polyvinyl alcohol sold under the name "MOWIOL 4088" by HOECHST | 1.2 g |
| Ethyl alcohol qs 10% (by volume) | |
| Spontaneous pH: 9.4 | |
| Preservative, perfume qs | |
| Water qs | 100 g |

The composition is packaged as described in Example 1.

The foam ($d = 0.076$ g/cm$^3$ at 20° C.) is applied on clean hair which has been wrung free of excess water. After drying, the hair has body and shape-retention.

EXAMPLE 5

An after-shampoo is prepared in the foam of an aerosol foam of the following composition:

| | |
|---|---|
| Adipic acid/dimethylaminohydroxy-propyldiethylenetriamine copolymer sold under the name "CARTARETIN F4" by SANDOZ | 3 g AS |
| Silicone cationic polymer sold under the name "DC 929 CATIONIC EMULSION" by DOW CORNING | 0.1 g AS |
| Polyvinyl alcohol sold under the name "MOWIOL 4088" by HOECHST | 2 g AS |
| HCl qs pH: 7 | |
| Preservative, perfume qs | |
| Water qs | 100 g |

The composition is packaged as described in Example 1.

This foam is applied after shampooing ($d = 0.066$ g/cm$^3$ at 20° C.) on hair which has been wrung free of excess water. After rinsing, the hair disentangles easily in the wet state and is light and has body in the dry state.

EXAMPLE 6

A non-rinsed aerosol foam having the following composition is prepared:

| | |
|---|---|
| Protein hydrolysate containing quaternary ammonium groups bearing at least one $C_1$-$C_{18}$ alkyl group, sold under the name "CROTEIN Q" by CRODA | 0.4 g AS |
| Quaternary polymer of vinylpyrrolidone and vinylimidazole, sold under the name "LUVIQUAT FC 370" by BASF | 0.3 g AS |
| Polyvinyl alcohol sold under the name "MOWIOL 1074" by HOECHST | 0.9 g AS |
| Ethyl alcohol qs 10% (by volume) | |
| Spontaneous pH: 5.7 | |
| Perfume, preservative qs | |

-continued

| Water qs | 100 g |

The composition is packaged as described in Example 1.

The foam obtained possesses a density d=0.065 g/cm³ at 20° C.

EXAMPLE 7

An after-shampoo is prepared in the form of an aerosol foam having the following composition:

| | |
|---|---|
| Distearyldimethylammonium chloride | 1 g AS |
| Quaternized protein designated "cocotrimonium collagen hydrolysate" in the CTFA dictionary and sold under the name "LEXEIN QX 3 000" by INOLEX | 0.5 g AS |
| Silicone cationic polymer sold under the name "DC 929 CATIONIC EMULSION" by DOW CORNING and containing 35% AS | 1 g AS |
| Polyvinyl alcohol sold under the name "MOWIOL 4088" by HOECHST | 1 g AS |
| NaOH qs pH: 7.3 | |
| Perfume, preservative qs | |
| Water qs | 100 g |

The composition is packaged as described in Example 1.

The foam (d=0.06 g/cm³ at 20° C.) is applied on hair which has been washed and wrung free of excess water. After being rinsed with water, the wet hair disentangles readily; the dry hair is soft and shiny.

EXAMPLE 8

An after-shampoo is prepared in the form of an aerosol foam having the following composition:

| | |
|---|---|
| Copolymer of dimethyldiallylammonium chloride and acrylamide of MW > 500,000, sold under the name "MERQUAT 550" by MERCK | 0.5 g AS |
| Cationic polymer described and prepared according to French Patent 2,270,846, consisting of repeated units of formula: | 0.5 g AS |

$$\left[ \begin{array}{cc} CH_3 & CH_3 \\ | & | \\ \oplus N-(CH_2)_3- \oplus N-(CH_2)_6 \\ | & | \\ CH_3 \; Cl^\ominus & CH_3 \; Cl^\ominus \end{array} \right]$$

| | |
|---|---|
| Methyl methacrylate/carboxymethyldimethylammonioethyl methacrylate copolymer prepared according to French Patent No. 2,470,596 | 0.5 g AS |
| Polyvinyl alcohol sold under the name "RHODOVIOL 45/140" by RHONE POULENC | 3 g AS |
| NaOH qs pH: 8 | |
| Perfume, preservative qs | |
| Water qs | 100 g |

The compositions is packaged as described in Example 1.

The foam (d=0.124 g/cm³ at 20° C.) is applied on hair which has been washed and wrung free of excess water. After rinsing and drying, the hair is lively and has body.

EXAMPLE 9

An after-shampoo is prepared in the form of an aerosol foam having the following composition:

| | |
|---|---|
| Distearyldimethylammonium chloride | 1 g AS |
| Silicone cationic polymer sold under the name "DC 929 CATIONIC EMULSION" by DOW CORNING and containing 35% AS | 1 g AS |
| Cationic polymer described and prepared according to French Patent 2,270,846, consisting of repeated units of formula: | 1 g AS |

$$\left[ \begin{array}{cc} CH_3 & CH_3 \\ | & | \\ \oplus N-(CH_2)_3- \oplus N-(CH_2)_6 \\ | & | \\ CH_3 \; Cl^\ominus & CH_3 \; Cl^\ominus \end{array} \right]$$

| | |
|---|---|
| Polyvinyl alcohol sold under the name "MOWIOL 4088" by HOECHST | 1 g AS |
| HCl qs pH: 7.6 | |
| Perfume, preservative qs | |
| Water qs | 100 g |

The composition is packaged as described in Example 1.

The foam (d=0.068 g/cm³ at 20° C.) is applied on clean hair which has been wrung free of excess water. After rinsing and drying, the hair is light and has body.

EXAMPLE 10

An after shampoo is prepared in the form of an aerosol foam having the following composition:

| | |
|---|---|
| Cetyl/stearyl (50:50) alcohol | 0.5 g AS |
| Synthetic spermaceti | 0.5 g |
| Docosyltrimethylammonium chloride sold under the name "GENAMIN KDM-F" by HOECHST | 0.7 g AS |
| Cationic emulsion sold by DOW CORNING under the name "DC 929 CATIONIC EMULSION" and containing 35% AS | 1.75 g AS |
| Polyvinyl alcohol sold under the name "MOWIOL 4088" by HOECHST | 2.0 g AS |
| Triethanolamine qs pH: 6.5 | |
| Preservative, perfume qs | |
| Water qs | 100 g |

96 g of this composition is pressurized in an integrally made aluminium aerosol can without a dip tube, equipped with a PRECISION P 73 valve, with 4 g of butane.

The foam obtained is creamy and has bulk. This foam is applied on clean hair which has been wrung free of excess water. After a few minutes' exposure and a rinse, the hair disentangles readily. After drying, it is soft and shiny and is easy to style.

EXAMPLE 11

An after-shampoo is prepared in the form of an aerosol foam having the following composition:

| | |
|---|---|
| Mixture of cetyl/stearyl alcohol and oxyethylenated cetyl/stearyl alcohol containing 15 mol of ethylene oxide | 1 g AS |
| Cetyl alcohol | 0.3 g AS |

-continued

| | |
|---|---|
| Synthetic spermaceti | 0.5 g |
| Docosyltrimethylammonium chloride sold under the name "GENAMIN KDM-F" by HOECHST | 0.56 g AS |
| Cationic emulsion sold by DOW CORNING under the name "DC 929 CATIONIC EMULSION", containig 35% AS | 1.75 g AS |
| Polyvinyl alcohol sold under the name "MOWIOL 4088" by HOECHST | 1.0 g AS |
| Triethanolamine qs pH: 6.5 | |
| Perservative, perfume qs | |
| Water qs | 100 g |

96 g of this composition is pressurized as described in Example 10.

The foam obtained, which has bulk and is creamy, is applied on clean hair hair which has been wrung free of excess water. After a few minutes' exposure and a rinse, the hair disentangles readily. After drying, it is soft and shiny and is easy to style.

EXAMPLE 12

The styling foam having the following composition is prepared:

| | |
|---|---|
| Vinyl acetate/crotonic acid/vinyl tert-butylbenzoate 65:10:25 copolymer, described in French Patent 2,439,798 | 1 g AS |
| Poly(vinylpyrrolidone/diethyl-aminoethyl methacrylate) copolymer sold in aqueous solution containing 20% AS under the name "COPOLYMERE 845" by GAF | 1 g AS |
| Polyvinyl alcohol sold under the name "MOWIOL 4088" by HOECHST | 1 g AS |
| 2-Amino-2-methyl-1-propanol qs pH: 8.5 | |
| Ethyl alcohol qs 10° | |
| Perfume, preservative qs | |
| Water qs | 100 g |

80 g of this composition is pressurized as described in Example 1, with 20 g of propellent.

The foam is applied on clean hair which has been wrung free of excess water. The wet hair disentangles readily and is soft to the touch. After drying, the hair is soft, smooth and lively, has shaped-retention and is easy to style.

The foam obtained possesses a density d=0.044 g/cm$^3$ at 20° C.

EXAMPLE 13

The styling foam having the following composition is prepared:

| | |
|---|---|
| Methyl methacrylate/carboxymethyl-dimethylammonioethyl methacrylate copolymer described in French Patent 2,470,596 | 0.4 g AS |
| Hydroxyethylcellulose copolymer grafted with diallyldimethyl-ammonium chloride, sold under the name "CELQUAT L 200" by NATIONAL STARCH | 0.5 g AS |
| Polyvinyl alcohol sold under the name "MOWIOL 4088" by HOECHST | 0.1 g AS |
| Perfume, perservative qs | |
| Ethyl alcohol qs 10° | |
| Water qs | 100 g |
| Spontaneous pH: 6 | |

85 g of this composition is pressurized as described in Example 1, with 15 g of propellent.

The foam is applied on clean hair which has been wrung free of excess water. The wet hair disentangles readily and is soft to the touch. After drying, the hair is soft, smooth and lively, has shape-retention and is easy to style.

The foam obtained possesses a density d=0.030 g/cm$^3$ at 20° C.

EXAMPLE 14

The anti-dandruff foam having the following composition is prepared:

| | |
|---|---|
| Poly($\beta$-alanine) | 0.2 g AS |
| Quaternized polyvinylpyrrolidone copolymer having an MW of 100,000, sold under the name "GAFQUAT 734" by GENERAL ANILINE | 0.1 g AS |
| 1-Hydroxypyridine-2-thione zinc salt sold under the name "OMADINE DE ZINC" by OLIN, containing 50% AS | 0.1 g AS |
| Polyvinyl alcohol sold under the name "MOWIOL 4088" by HOECHST | 1.5 g AS |
| Perfume, preservative qs | |
| Water qs | |
| Spontaneous pH: 7.3 | |

85 g of this composition is pressurized as described in Example 1, with 15 g of propellent.

The foam is applied on clean hair which has been wrung free of excess water. The wet hair disentangles readily and is soft to the touch. After drying, the hair is soft, smooth and lively, has shape-retention and is easy to style.

The foam obtained possesses a density d=0.048 g/cm$^3$ at 20° C.

EXAMPLE 15

The styling foam having the following composition is prepared:

| | |
|---|---|
| Tetradecyltrimethylammonium bromide | 0.2 g AS |
| Polyvinyl alcohol sold under the name "MOWIOL 4-98" by HOECHST and etherified with 2.24 mol % of bromooctane | 3.2 g AS |
| Poly(dimethylbutenylammonium chloride)-$\alpha$, $\omega$-bis(triethanolammonium chloride) sold under the name "ONAMER M" by ONYX INTERNATIONAL | 0.1 g AS |
| Perfume, colouring, preservative qs, | |
| Water qs | 100 g |
| Spontaneous pH: 6.5 | |

90 g of this composition is pressurized as described in Example 1, with 10 g of propellent.

The foam is applied on clean hair which has been wrung free of excess water. The wet hair disentangles readily and is soft to the touch. After drying, the hair is soft, smooth and lively, has shape-retention and is easy to style.

The foam obtained possesses a density d=0.039 g/cm$^3$ at 20° C.

EXAMPLE 16

A foam for blow-drying having the following composition is prepared:

| | |
|---|---|
| Cationic emulsion sold by DOW CORNING under the name "DC 929 CATIONIC EMULSION" at a concentration of 35% AS | 0.7 g AS |
| Polyoxyethylenated and/or polyoxypropylenated dimethylsiloxane polymer, sold under the name "DOW CORNING 193 SURFACTANT" by DOW CORNING | 0.7 g AS |
| Polyvinyl alcohol sold under the name "MOWIOL 4088" by HOECHST Spontaneous pH: 5 | 0.5 g |
| Perfume, preservative qs | |
| Water qs | 100 g |

90 g of this composition is pressurized as described in Example 1, with 10 g of propellent.

After application of the foam on the hair, the latter becomes soft, smooth and lively, has shape-retention and is easy to style.

EXAMPLE 17

An after-shampoo having the following composition is prepared:

| | |
|---|---|
| Ethylenebis[N,N—dimethyl(oleyl/cetyl)acetamide] dichloride described in French Patent 2,464,710 | 0.3 g AS |
| Polyvinyl alcohol sold under the name "MOWIOL 4088" by HOECHST | 6 g |
| Perfume, preservative qs | |
| Water qs | 100 g |
| Triethanolamine qs pH: 7.5 | |

90 g of this composition is pressurized as described in Example 1, with 10 g of propellent.

The foam is applied on the hair, which is then shiny, soft and easy to disentangle.

The foam obtained possesses a density d=0.084 g/cm$^3$ at 20° C.

EXAMPLE 18

An after-shampoo having the following composition is prepared:

| | |
|---|---|
| Poly(dimethylbutenylammonium chloride)-α, ω-bis(triethanolammonium chloride) sold under the name "ONAMER M" by ONYX INTERNATIONAL | 5 g AS |
| Polyvinyl alcohol sold under the name "MOWIOL 4088" by HOECHST | 5 g AS |
| Perfume, preservative qs | |
| Water qs | 100 g |
| Triethanolamine qs pH 6 | |

90 g of this composition is pressurized as described in Example 1, with 10 g of propellent.

When applied on the hair, the composition enables the latter to be disentangled easily and also enables the condition of the ends of damaged hair to be improved.

EXAMPLE 19

An after-shampoo having the following composition is prepared:

| | |
|---|---|
| Poly(vinylpyrrolidone/diethylaminoethyl methacrylate) copolymer, sold in aqueous solution containing 20% AS under the name "COPOLYMER 845" by GAF | 1 g AS |
| Copolymer of dimethyldiallylammonium chloride and acrylamide, of MW >500,000, sold under the name "MERQUAT 550" by MERCK | 0.03 g AS |
| Polyvinyl alcohol sold under the name "MOWIOL 4088" by HOECHST | 2 g |
| Perfume, preservative qs | |
| Water qs | 100 g |
| Triethanolamine qs pH: 6.5 | |

90 g of this composition is pressurized as described in Example 1, with 10 g of propellent.

The composition is applied on the hair which, after drying, has good shape-retention and body.

The foam obtained possesses a density d=0.158 g/cm$^3$ at 20° C.

EXAMPLE 20

An after-shampoo having the following composition is prepared:

| | |
|---|---|
| Poly(vinylpyrrolidone/diethylaminoethyl methacrylate) copolymer, sold in aqueous solution containing 20% AS under the name "COPOLYMER 845" by GENERAL ANILINE | 3 g AS |
| Quaternized polyvinylpyrrolidone copolymer having an MW of 1,000,000, sold at a concentration of 20% AS under the name "GAFQUAT 755" by GENERAL ANILINE | 1 g AS |
| Polyvinyl alcohol sold under the name "MOWIOL 4088" by HOECHST | 3 g |
| Perfume, preservative qs | |
| Water qs | 100 g |
| Triethanolamine qs pH: 7 | |

90 g of this composition is pressurized as described in Example 1, with 10 g of propellent.

The foam is applied on clean hair which has been wrung free of excess water. After drying, the hair has body and shape-retention.

The foam obtained possesses a density d=0.128 g/cm$^3$ at 20° C.

EXAMPLE 21

An after-shampoo having the following composition is prepared:

| | |
|---|---|
| Condensate of piperazine and epichlorohydrin, prepared according to Example 1 of French Patent 2,162,025 | 1.5 g AS |
| Sodium polyvinylsulphonate | 0.6 g AS |
| Polyvinyl alcohol sold under the name "MOWIOL 4088" by HOECHST | 5 g |
| Perfume, preservative qs | |
| Water qs | 100 g |
| Hydrochloric acid qs pH: 8.3 | |

90 g of this composition is pressurized as described in Example 1, with 10 g of propellent.

The foam is applied on clean hair which has been wrung free of excess water. After drying, the hair has shape-retention and is lively.

The foam obtained possesses a density d=0.098 g/cm$^3$ at 20° C.

We claim:

1. An aqueous cosmetic composition for the treatment of the hair or the skin, in the form of a foam from an aerosol device in which it is packaged under pressure, in the presence of a propellant agent, comprising, in a cosmetically acceptable aqueous medium containing one or more cosmetic products for the cosmetic treatment of the hair or the skin, at least one partially acetylated polyvinyl alcohol containing at least units of formulae (I) and (II)

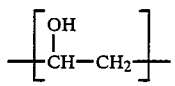

(I)

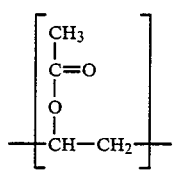

(II)

in which the units of formula (II) are present in proportions of greater than or equal to 3 mol % with respect to the totality of units in the polymer, this polymer possessing a viscosity at a concentration of 4% in water at 20 degrees C. of between 0.005 and 0.065 Pa.s.

2. Composition according to claim 1, wherein the partially acetylated polyvinyl alcohol forms a foam, after expansion in the air from an aerosol device containing a 1% strength aqueous solution of the said partially acetylated polyvinyl alcohol, having a density of less than or equal to 0.3 g/cm$^3$ at 20° C.

3. Composition according to claim 1, wherein that the partially acetylated polyvinyl alcohol contains from 97 to 60% of units of formula (I).

4. Composition according to claim 1, wherein the partially acetylated polyvinyl alcohol is employed in proportions of between 0.05 and 8% by weight relative to the total weight of the composition.

5. Composition according to claim 1, wherein the aqueous cosmetic medium contains water or a mixture of water and a cosmetically acceptable solvent which is present in an amount such as to enable a foam having a density of less than or equal to 0.3 g/cm$^3$ at 20° C. to be obtained with the partially acetylated polyvinyl alcohol.

6. Composition according to claim 1, further containing treatment agents for the hair or the skin which are cationic, anionic, nonionic or amphoteric in nature.

7. Composition according to claim 6, wherein the cationic surfactant are selected from the group comprising
(1) the compounds of formula:

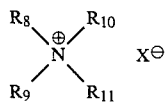

in which $R_8$ and $R_{11}$ each denote a mixture of alkenyl and/or alkyl radicals derived from tallow fatty acids having 14 to 22 carbon atoms and $R_9$ and $R_{10}$ denote a methyl radical, $X^\ominus$ denoting $Cl^\ominus$, or alternatively $R_8$ denotes a $C_{18}$ alkyl radical and $R_{11}$ denotes a benzyl radical, $R_9$ and $R_{10}$ denoting a methyl radical and $X^\ominus$ denotes $Cl^\ominus$, or alternatively (2) bis(quaternary ammonium) derivatives bearing an ester group
(3) quaternary ammonium derivatives corresponding to the formula:

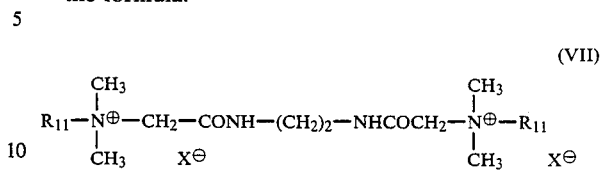

where $R_{11}$ is a tallow chain and $X^\ominus$ is $Cl^\ominus$,

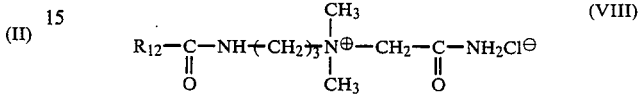

where the radical $R_{12}$ is a coconut chain
(4) (tallow alkyl)trimethylammonium chloride
(5) tetradecyltrimethylammonium bromide
(6) the (acrylamidopropyl)dimethylethylammonium ethylsulphate in which the acyl group is derived from lanolin fatty acids
(7) (γ-gluconamidopropyl)dimethylhydroxyethylammonium chloride
(8) trimethyldocosylammonium chloride.

8. Composition according to claim 6, wherein the cationic polymer is selected from the group comprising:
(1) vinylpyrrolidone/dialkylaminoalkyl acrylate or methacrylate copolymers, quaternized or otherwise;
(2) cellulose ether derivatives containing quaternary ammonium groups;
(3) copolymers of cellulose or of cellulose derivatives grafted with a water-soluble quaternary ammonium monomer;
(4) cationic polysaccharides;
(5) polymers consisting of piperazinyl units and of divalent alkylene or hydroxyalkylene radicals having a linear of branched chain optionally interrupted by oxygen, sulphur or nitrogen atoms or by aromatic or heterocyclic rings, as well as the oxidation and/or quaternization products of these polymers;
(6) the polyaminoamide derivatives resulting from the condensation of a polyalkylenepolyamine with polycarboxylic acids, followed by a crosslinking and/or an alkylation with bifunctional agents;
(7) cyclopolymers of dialkyldiallylammonium chloride;
(8) quaternary polymers of vinylpyrrolidone and vinylimidazole;
(9) the poly(quaternary ammonium) polymers containing repeated units corresponding to the formula:

in which $R_{13}$ and $R_{14}$, $R_{15}$ and $R_{16}$, which may be identical or different, denote aliphatic, alicyclic or arylaliphatic radicals containing from 1 to 20 carbon atoms or lower hydroxyalkylaliphatic radicals, or alternatively $R_{13}$ and $R_{14}$ and $R_{15}$ and $R_{16}$, together or separately, form, with the nitrogen atoms to which they are attached, heterocyclic systems optionally containing a second hetero atom other than nitrogen, or alternatively $R_{13}$, $R_{14}$, $R_{15}$ and $R_{16}$ denotes a linear or branched $C_1$-$C_6$ alkyl radical substituted with a nitrile, ester, acyl or amide group or with a group $$-\overset{O}{\underset{\|}{C}}-O-R_{17}-D \text{ or } -\overset{O}{\underset{\|}{C}}-NH-R_{17}-D$$

where $R_{17}$ is an alkylene and D a quaternary ammonium;

$A_2$ and $B_2$ denote polymethylene groups containing from 2 to 20 carbon atoms, which may be linear or branched, saturated or unsaturated and may contain, linked to or inserted in the main chain, one or more aromatic rings, or one or more oxygen or sulphur atoms, or sulphoxide, sulphone, disulphide, amino, alkylamino, hydroxyl, quaternary ammonium, ureido, amide or ester groups, and $X^{\ominus}$ denotes an anion derived from an inorganic or organic acid.

$A_2$ and $R_{13}$ and $R_{15}$ can form a piperazine ring with the two nitrogen atoms to which they are attached; in addition, if $A_2$ denotes a saturated or unsaturated, linear or branched alkylene or hydroxyalkylene radical, $B_2$ can also denote a group:

$$-*CH_2)_n-CO-D-OC-(CH_2)_n-$$

in which D denotes:
(a) a glycol residue of formula: $-O-Z-O-$ where Z denotes a linear or branched hydrocarbon radical or a group corresponding to the formula:

$$+CH_2-CH_2-O+_{\overline{x}}CH_2-CH_2-$$

$$-\left[CH_2-\underset{\underset{CH_3}{|}}{CH}-O\right]_y-CH_2-\underset{\underset{CH_3}{|}}{CH}-$$

where x and y denote an integer from 1 to 4 representing a definite and unique degree of polymerization, or any number from 1 to 4 representing an average degree of polymerization;
(b) a bis(secondary diamine) residue such as a piperazine derivative;
(c) a bis(primary diamine) residue of formula:

$$-NH-Y-NH-$$

where y denotes a linear or branched hydrocarbon radical or alternatively a divalent radical $$-CH_2-CH_2-S-S-CH_2-CH_2-$$

(d) a ureylene group of formula:

$$-NH-CH-NH-;$$

$X^{\ominus}$ is an anion such as chloride or bromide;
(10) the poly(quaternary ammonium) polymers consisting of units of formula:

$$\overset{R_{18}}{\underset{\underset{R}{|}}{\overset{|}{\oplus}N}}+CH_2)_{\overline{x}}NH-\overset{O}{\underset{\|}{C}}+CH_2)_{\overline{m}}\overset{O}{\underset{\|}{C}}-NH+CH_2)_{\overline{y}}\overset{R_{20}}{\underset{\underset{R_{21}}{|}}{\overset{|}{N^{\oplus}}}}A- \quad \text{(XVIII)}$$
$$X^{\ominus} \qquad X^{\ominus}$$

in which $R_{18}$, $R_{19}$, $R_{20}$ and $R_{21}$, which may be identical or different, denote a hydrogen atom or a methyl, ethyl, propyl, β-hydroxyethyl, β-hydroxypropyl or $-CH_2CH_2(OCH_2CH_2)_pOH$ radical, where p equals 0 and an integer between 1 and 6, with the proviso that $R_{18}$, $R_{19}$, $R_{20}$ and $R_{21}$ do not simultaneously denote a hydrogen atom; x and y, which may be identical or different, are integers between 1 and 6;
m equals 0 or an integer between 1 and 34,
X denotes a halogen atom,
A denotes a radical of a dihalide and preferably denotes $$-CH_2-CH_2-O-CH_2-CH_2-$$

(11) the homopolymers or copolymers derived from acrylic or methacrylic esters or amides and containing the units:

$$-CH_2-\underset{\underset{\underset{\underset{\underset{R_{22}}{\diagup}\underset{R_{23}}{\diagdown}}{N}}{A_1}}{\underset{\|}{C=O}}}{\overset{R_{24}}{\underset{|}{C}}}-\text{, }-CH_2-\underset{\underset{\underset{R_{25} X_2^{\ominus}}{R_{26}-N^{\oplus}-R_{27}}}{\underset{A_1}{|}}}{\overset{R_{24}}{\underset{\underset{\|}{C=O}}{\underset{|}{C}}}}-\text{ or }-CH_2-\underset{\underset{\underset{R_{25} X_2^{\ominus}}{R_{26}-N^{\oplus}-R_{27}}}{\underset{A_1}{|}}}{\overset{R_{24}}{\underset{\underset{\|}{C=O}}{\underset{|}{\underset{NH}{C}}}}}-$$

in which $R_{24}$ denotes H or $CH_3$,
$A_1$ is a linear or branched alkyl group having from 1 to 6 carbon atoms or a hydroxyalkyl group having from 1 to 4 carbon atoms,
$R_{25}$, $R_{26}$ and $R_{27}$, which may be identical or different, denote an alkyl group having from 1 to 18 carbon atoms or a benzyl radical,
$R_{22}$ and $R_{23}$ denote hydrogen or an alkyl group having from 1 to 6 carbon atoms, and
$X_2^-$ denotes a methosulphate anion or a halide such as chloride or bromide;
(12) a polyamine classified under the name "polyethylene glycol (15) tallow polyamine".

9. Composition according to claim 6, containing cationic treatment agents which are cationic surfactants or cationic polymers having a molecular weight of between 500 and 5,000,000.

10. Composition according to claim 9, wherein the cationic surfactant are:
(1) salts of fatty amines, quaternary ammonium salts, lactates of N,N-dimethylamino or N,N-diethylamino polyoxyethylcarboxylate, alkylpyridinium salts, imidazoline derivatives and amine oxides,
(2) cationic derivatives corresponding to the formula:

$$R'O+C_2H_3O(CH_2OH)+_{\overline{n}}CH_2-CHOH-CH_2-N\overset{R''}{\underset{R'''}{\diagdown}} \quad \text{(III)}$$

in which R' denotes a saturated or unsaturated, linear or branched alkyl radical or an alkylaryl radical having a linear or branched chain containing from 8 to 22 carbon atoms, R" and R''' denote lower hydroxyalkyl radicals or alkylene radicals joined to one another to form a heterocyclic system, and n is a number between 0.5 and 10,
(3) bis(quaternary ammonium) derivatives having two lipophilic chains, of formula (V):

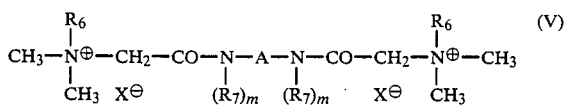

in which $R_6$ denotes a linear or branched, saturated or unsaturated aliphatic group having from 8 to 22 carbon atoms or a mixture of these groups or a mixture of lipophilic chains derived from natural products having from 8 to 30 carbon atoms; A denotes a group $-(CH_2)-_n$ in which n denotes an integer from 1 to 18 and $R_7$ denotes H, and m=1; and A can also form a heterocyclic group with the nitrogen atoms to which it is attached, in which case m=0 and $X^\ominus$ denotes an anion derived from an inorganic or organic acid, (4) compounds of formula:

in which:
(a) When $R_1$ denotes a group of formula:

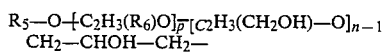

in which $R_5$ denotes a saturated or unsaturated, linear or branched aliphatic radical, $R_6$ is an alkyl radical, a linear or branched alkoxymethyl radical or a linear alkenyloxy radical, p denotes an integer or decimal number from 1 to 2.5, n denotes an integer or decimal number from 2 to 20, $R_2$ denotes an alkyl or hydroxyalkyl radical having from 1 to 3 carbon atoms and $R_3$ and $R_4$, which may be identical or different, denote an alkyl or hydroxyalkyl radical having from 1 to 3 carbon atoms or alternatively form, with the nitrogen atom to which they are attached, a 5-or 6-membered heterocyclic system; $X^\ominus$ denotes an anion, (b) When $R_2$ and $R_3$ denote a methyl radical, $R_1$ and $R_4$ have the following meanings:
(i) $R_1$ and $R_4$ denote a linear aliphatic radical;
(ii) or alternatively $R_1$ denotes a saturated linear aliphatic radical and $R_4$ denotes a methyl or benzyl radical;
(iii) or alternatively $R_1$ denotes an alkylamidopropyl ($C_{14}-C_{22}$ alkyl) radical and $R_4$ denotes and alkyl acetate ($C_{12}-C_{16}$ alkyl) group;
$X^\ominus$ denotes an anion such as a halide or $CH_3SO_4^\ominus$;

(c) When $R_1$ denotes an alkylamidoethyl and/or alkenylamidoethyl group in which the alkyl and/or alkenyl radical containing from 14 to 22 carbon atoms is derived from tallow fatty acids, $R_2$ and $R_3$ form with the nitrogen a substituted heterocyclic system of the 4,5-dihydroimidazole type,
$R_4$ denotes a $C_1-C_4$ alkyl;
$X^\ominus$ denotes a $CH_3SO_4^\ominus$ anion.

11. Composition according to claim 9, wherein the cationic polymer is a quaternized protein consisting of a chemically modified polypeptide bearing quaternary ammonium groups at the end of the chain or grafted onto the latter.

12. Composition according to claim 9, wherein the cationic polymer is a silicone cationic polymer.

13. Composition according to claim 9, wherein the cationic polymer is a polyamine, polyaminoamide or a poly(quaternary ammonium) compounds.

14. Composition according to claim 1, containing an anionic polymer having a molecular weight of between 500 and 5,000,000 and containing carboxylic, sulphonic or phosphoric units.

15. Composition according to claim 14, wherein the anionic polymer is an alkali metal salt of polyhydroxycarboxylic acids; a homopolymer of acrylic or methacrylic acid and their salts; methacrylic acid/$C_1-C_4$ alkyl methacrylate copolymers; copolymers derived from maleic, fumaric and itaconic acids or anhydrides and from vinyl esters, vinyl ethers, vinyl halides, phenylvinyl derivatives, acrylic acid or acrylates, these copolymers optionally being completely or partially esterified; copolymers of maleic, fumaric and itaconic anhydrides and of an allyl or methallyl ester, and optionally of another monomer, in which the anhydride functions can be monoesterified or monoamidated; vinyl acetate/crotonic acid copolymer grafted onto polyethylene glycol; vinyl acetate/ crotonic acid/vinyl neodecanoate terpolymer, vinyl acetate/ crotonic acid/vinyl tert-butylbenzoate terpolymer, polyacrylamides containing carboxylate groups; the sodium salts of polystyrenesulphonic acid, polyacrylamido-sulphonic acid salts, salts of polymers containing alkylnaphthalenesulphonic acid units, sodium or calcium lignosulphonates; and sodium polyvinylsulphonates.

16. Composition according to claim 1, further containing nonionic polymers having a molecular weight of between 500 and 3,000,000.

17. Composition according to claim 1, further containing amphoteric polymers having a molecular weight of between 500 and 3,000,000.

18. Composition according to claim 17, wherein the amphoteric polymer is selected from the group comprising
the polymers resulting from the reaction of a polyaminoamide, obtained by polycondensation of adipic acid, and diethylenetriamine in equimolar amounts, and crosslinked with epichlorohydrin in the proportion of 11 mol of crosslinking agent for 100 secondary amine groups of the polyaminoamide, the product being alkylated with propane sultone or alternatively with sodium chloroacetate;
the polymer obtained by polycondensation of epichlorohydrin and piperazine in the presence of sodium hydroxide, and betainized;
octylacrylamide/acrylate/butylaminoethyl methacrylate copolymer;
methyl methacrylate/carboxymethyldimethylammonioethyl methacrylate copolymer;
($C_1-C_{18}$) alkyl methacrylate/carboxymethyldimethylammoniomethyl methacrylate copolymer;
polymers derived from chitosan;
the polyaspartic acid derivatives corresponding to the formula:

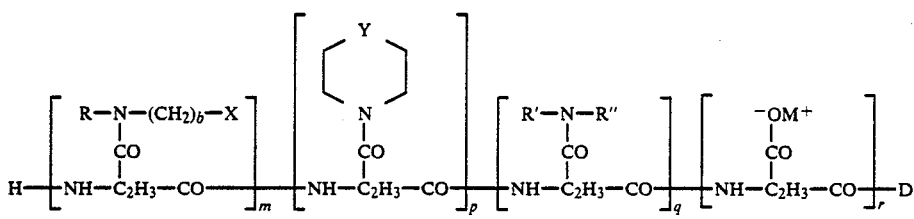

(XVIII)

in which R denotes a hydrogen atom or a lower alkyl radical, b is an integer varying from 2 to 6, X denotes a group $-NR_I(R_{II})$ or a group $-N^{\oplus}R_I(R_{II})(R_{III})Z^{\ominus}$ where $R_I$, $R_{II}$ and $R_{III}$, which may be identical or different, denote a hydrogen atom, an alkyl group having 1 to 18 carbon atoms or an alkenyl group having 2 to 18 carbon atoms, or $R_I$ and $R_{II}$ denote, with the nitrogen atom to which they are attached, a 6-membered ring which can contain another hetero atom, and $Z^{\ominus}$ denotes an anion derived from an organic or inorganic acid, Y denotes an oxygen atom, a methylene group, a group NR''' or a group $N^{\oplus1}(R''')(R'''')Z_1^{\ominus}$, where R''' and R'''', which may be identical or different, denote a hydrogen atom, an alkyl group having 1 to 18 carbon atoms or an alkenyl group having 2 to 18 carbon atoms and $Z_1^{\ominus}$ denotes an anion derived from an organic or inorganic acid, R' denoting a hydrogen atom, a lower hydroxyalkyl group, a lower hydroxyalkyloxyalkyl group, an alkyl group having 1 and 18 carbon atoms or an alkenyl group having 2 to 18 carbon atoms, R'' denotes a hydrogen atom, a lower hydroxyalkyl group or a lower alkyl group, $M^{\oplus1}$ denotes a hydrogen atom, an alkali metal atom or an alkaline earth metal half-atom, or alternatively $M^{\oplus}$ denotes an ammonium ion, and D denotes a group

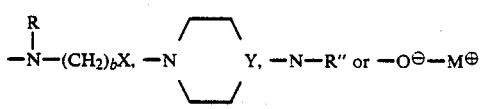

m and p, q and r denoting integers including 0, such that the sum m+p+q+r varies from 15 to 500, m and p being able to be zero simultaneously a) only when q is other than 0 and R' denotes a hydroxyalkyl group, and b) when q equals 0.

19. Composition according to claim 1, containing in addition to the partially acetylated polyvinyl alcohol, at least one water-dispersible cationic surfactant, at least one water-soluble quaternized protein and at least one silicone cationic polymer.

20. Composition according to claim 1, containing in the presence of the partially acetylated polyvinyl alcohol, at least one water-dispersible cationic surfactant, at least one water-soluble quaternized cationic polymer of the poly(quaternary ammonium) type and at least one silicone cationic polymer.

21. Composition according to claim 1, containing in addition to the partially acetylated polyvinyl alcohol, at least one sodium polyvinylsulphonate and a polymer which is a condensate of piperazine and epichlorohydrin.

22. Composition according to claim 1, containing in addition to the partially acetylated polyvinyl alcohol, at least one amphoteric polymer consisting of methyl methacrylate/carboxymethyldimethylammonioethyl methacrylate and a cationic polymer chosen from
(a) cellulose ether derivatives containing quaternary ammonium groups
(b) polymers of cellulose and of cellulose derivatives grafted with a water-soluble quaternary ammonium monomer
(c) homopolymers of dimethyldiallylammonium chloride or copolymers of dimethyldiallylammonium chloride with acrylamide
(d) quaternary polymers of vinylpyrrolidone and vinylimidazole, and
(e) vinylpyrrolidone/diaminoalkyl acrylate or methacrylate copolymers, quaternized or otherwise.

23. Composition according to claim 1, containing in addition to the partially acetylated polyvinyl alcohol, a vinylpyrrolidone/diethylaminoethyl methacrylate copolymer.

24. Composition according to claim 1, containing in addition to the partially acetylated polyvinyl alcohol, a vinylpyrrolidone/diethylaminoethyl methacrylate copolymer and a cationic polymer chosen from cellulose ether derivatives containing quaternary ammonium groups and polymers of cellulose or cellulose derivatives grafted with a water-soluble quaternary ammonium monomer, homo- or copolymer of dimethyldiallylammonium chloride or quaternary copolymers of vinylpyrrolidone and vinylimidazole.

25. Composition according to claim 1, containing in aqueous or aqueous-alcoholic dispersion, a partially acetylated polyvinyl alcohol, a water-soluble polyamide and a cationic polymer chosen from cellulose ether derivatives containing quaternary ammonium groups, copolymers of cellulose and of cellulose derivatives grafted with a water-soluble quaternary ammonium monomer, dimethyldiallylammonium polymers, quaternary polymers of vinylpyrrolidone and vinylimidazole, and vinylpyrrolidone/diaminoalkyl acrylate or methacrylate copolymers, quaternized or otherwise.

26. Composition according to claim 1, wherein the treatment agent is present in proportions of between 0.01 and 10% by weight relative to the total weight of the composition.

27. Composition according to claim 1, containing electrolytes which are sulphates, halides or the alkali metal or alkaline earth metal salts of organic acids, in proportions of between 0.25 and 8% by weight relative to the total weight of the composition.

28. Composition according to claim 1, also containing perfumes, colourings whose function is to colour the composition itself or the hair or the skin, preservatives, sequestering agents, anti-grease, anti-seborrhoeic or anti-dandruff agents, silicones, demulcents, sunscreens or peptizing agents.

29. Composition according to claim 1, also containing anionic, nonionic or amphoteric surfactants, or mixtures thereof, in proportions not exceeding 10%.

30. Use of the composition according to claim 1, as an after-shampoo composition, a foam to be rinsed which is to be applied before or after dyeing and bleaching, before or after permanent waving or straightening, a setting or blow-drying foam, a non-rinsed foam, or a restructuring, permanent waving, dyeing or bleaching composition.

31. Process for the cosmetic treatment of the hair or the skin, wherein at least one foam resulting from the expansion in the air of the composition as defined in claim 1, is applied on the skin or the hair.

* * * * *